United States Patent [19]

Ueno et al.

[11] Patent Number: 5,137,915
[45] Date of Patent: Aug. 11, 1992

[54] PROSTAGLANDINS OF THE D SERIES, AND TRANQUILIZERS AND SOPORIFICS CONTAINING THE SAME

[75] Inventors: Ryuzo Ueno, Nishinomiya; Ryuji Ueno, Kyoto; Ichie Kato, Kawanishi; Tomio Oda, Itami, all of Japan

[73] Assignee: K.K. Ueno Seiyaku Oyo Kenkyujo, Osaka, Japan

[21] Appl. No.: 715,151

[22] Filed: Jun. 13, 1991

Related U.S. Application Data

[60] Division of Ser. No. 403,774, Sep. 6, 1989, Pat. No. 5,073,569, which is a continuation-in-part of Ser. No. 149,272, Jan. 28, 1988, abandoned.

[30] Foreign Application Priority Data

Jun. 28, 1987 [JP]  Japan ................................ 62-18821

[51] Int. Cl.$^5$ ................... C07C 170/00; A01K 31/557
[52] U.S. Cl. .................................. 514/530; 514/573; 560/121; 562/503
[58] Field of Search ......................... 560/121; 562/503; 514/530, 573

[56] References Cited

U.S. PATENT DOCUMENTS

5,001,153  3/1991  Ueno ........................... 514/530

FOREIGN PATENT DOCUMENTS

2272641  12/1975  France .

OTHER PUBLICATIONS

Chemical Abstracts, vol 86, No. 11 Mar. 14, 1977, p. 69, Abstract No. 65891m, Columbus, Ohio.
Chemical Abstracts, vol. 102, No. 19, May 13, 1985, p. 125, Abstract No. 161123g, Columbus, Ohio.
Biochemical and Biophysical Research Communications vol. 109, No. 2, 1982, pp. 576-582.

*Primary Examiner*—Robert Gerstl
*Attorney, Agent, or Firm*—Sughrue, Mion, Zinn, Macpeak & Seas

[57] ABSTRACT

The present invention provides novel prostaglandins D, that is, 13,14-dihydro-15-keto-PGDs, which have an excellent sedative and sleep-inducing activity, and so they are useful for tranquilizer and/or soporifics.

60 Claims, 24 Drawing Sheets

PROSTAGLANDINS OF THE D SERIES, AND TRANQUILIZERS AND SOPORIFICS CONTAINING THE SAME

This application is a divisional application of Ser. No. 07/403,774 filed Sept. 6, 1989, U.S. Pat. No. 5,073,569, in turn a continuation-in-part application of Ser. No. 07/149,272 filed Jan. 28, 1988, the latter abandoned.

BACKGROUND OF THE INVENTION

The present invention relates to novel prostaglandins of D series (referred to as prostaglandins D or PGDs hereafter), and tranquilizers and soporifics containing the compound.

Prostaglandin is a general name for prostanoic acids which is divided in E, F, A, B, C, D, H and the like according to the way keto or hydroxyl group introduced in five membered ring portions. In addition to stimulating uterine muscle, prostaglandins have various physiological and pharmacological activities such as vasodilation, inhibition of blood-platelet aggregation, anti-inflammatory effect and the like.

Prostaglandin D contains the following five membered ring:

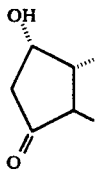

classifying roughly, $PGD_2$ wherein $C_5-C_6$ bond is double bond:

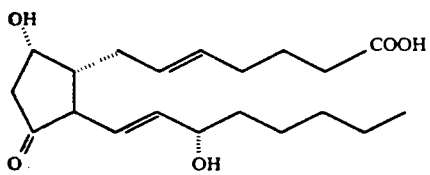

and $PGD_3$ wherein $C_{17}-C_{18}$ bond is double bond;

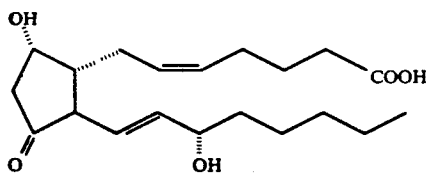

are known. For example, $PGD_2$ is known to have activities such as analgesic activity, sedative activity, induction of sleep, thermoregulation and the like. However, activity which $PGD_2$ may show greatly depends on the administration route thereof. For example, experiments using rats show that physiological sleep can not be induced by peripheral administration such as subcutaneous injection, intravenous injection, oral administration and the like but induced by administrating directly in the cerebral ventricle. Therefore, $PGD_2$ is difficult to administrate. In addition, $PGD_2$ also exhibits inhibition of blood-platelet aggregation, bronchoconstriction, constriction of enteron muscle, vasodilation and the like as well as side-effect such as severe diarrhea. Therefore, there exist problems to use $PGD_2$ as tranquilizers and soporifics.

On the other hand, in metabolites of human or animal, the existence of analogues of prostaglandins D in the free form wherein carbons at 13 and 14 positions are saturated and that at 15 position forms carbonyl group is confirmed. These 13,14-dihydro-15-keto-prostaglandins D are

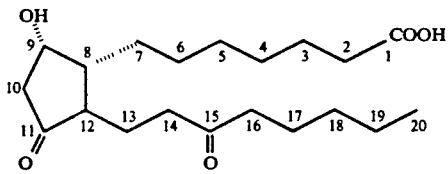

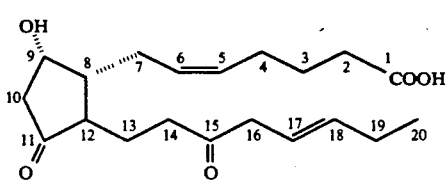

and the corresponding $PGD_1$ and $PGD_2$ and, $PGD_3$ are known as metabolites which are naturally produced in vivo by enzymatic metabolism. These 13,14-dihydro-15-keto-PGDs have been reported as physiologically and pharmacologically inert metabolites which barely exhibit various physiological activities that PGDs usually do (Accta Physiologica Scandinavica, 66, 509–(1966)).

SUMMARY OF THE INVENTION

In the course of study on the pharmacological activities of the above metabolites, 13,14-dihydro-15-keto-$PGD_2$, the present inventor has found that 13,14-dihydro-15-keto-$PGD_2$ exhibits sedative and sleep induction effect by intra-postcisternal and intracerebroventricular administration, respectively. Further, while estimating pharmacological activities of 13,14-dihydro-15-keto-PGDs derivatives, I have found that 13,14-dihydro-15-keto-PGD analogues exhibit sedative and sleep induction effect, which is one of the pharmacological activities of -PGDs, by peripheral administration such as subcutaneous injection, intravenous injection, oral administration as well as intraventricular administration, when they are converted into the corresponding compounds wherein carboxylic acid is esterified, or salts thereof and those in the free form or having a protective group, which contain substitutents at 16, 17, 19 and/or 20 position, those with methyl or hydroxymethyl group at 9 position, those with alkoxy group at the end of ω-chain and those with triple bond at the end of ω-chain and those with triple bond at carbons at 5 and 6 positions. Moreover, I have found that 13,14-dihydro-15-keto-PGD analogues never or barely exhibit pharmacological and physiological activities such as inhibition of blood-platelet aggregation, bronchoconstriction, constriction of enteron, vasodilation and the like, which PGDs usually have, and they are not accompanied with side effect.

BRIEF DESCRIPTION OF THE INVENTION

DETAILED DESCRIPTION OF THE INVENTION

Figure 1:
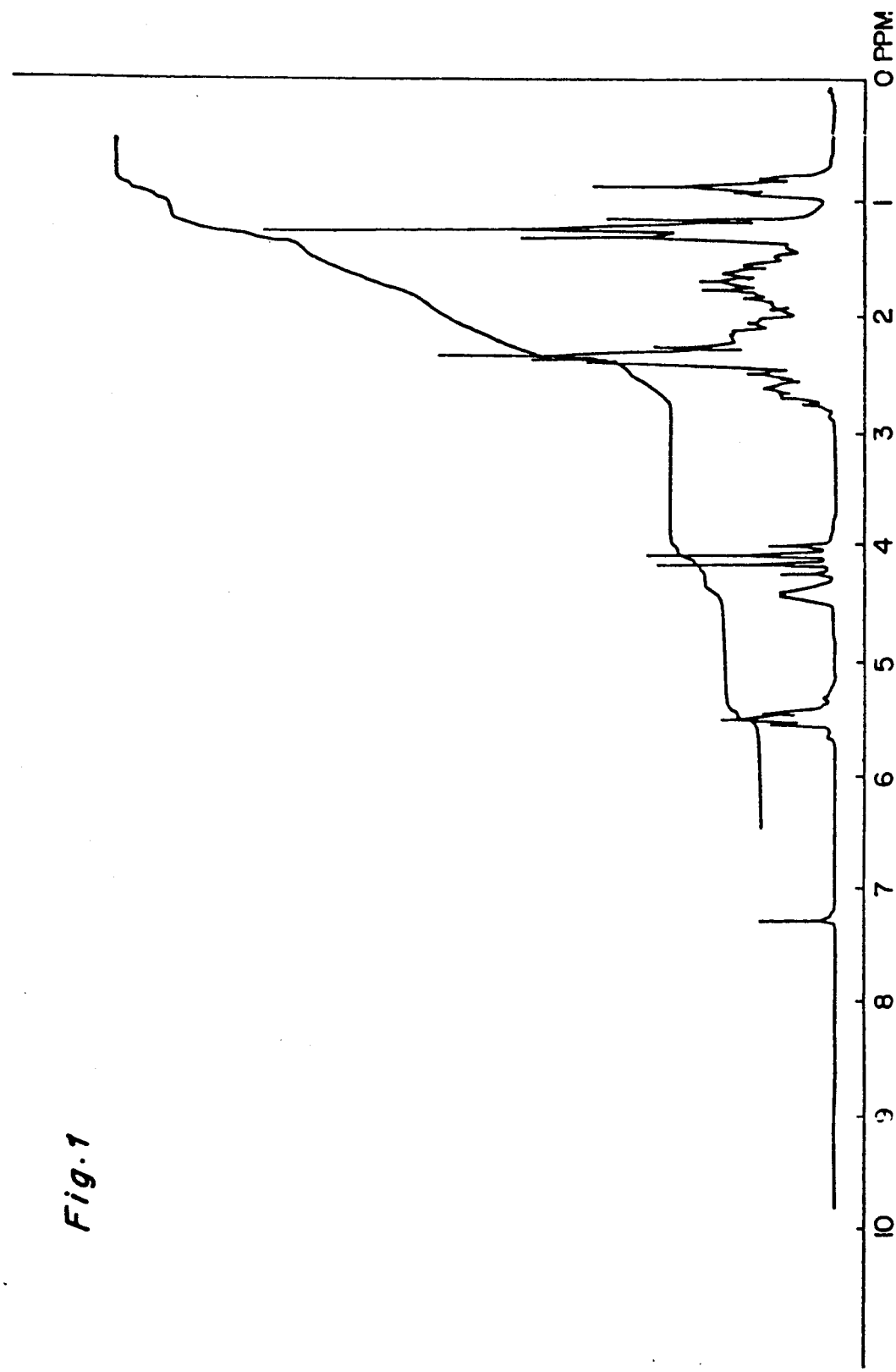
FIG. 1–FIG. 22 show the n.m.r. spectrum of 13,14-dihydro-15-keto-PGDs derivatives of the present invention.

The present invention provides prostaglandins D represented by the general formula:

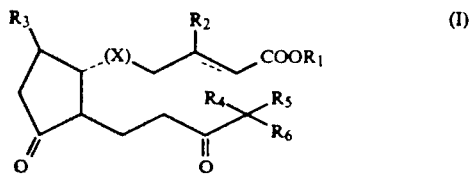

wherein
(X) is

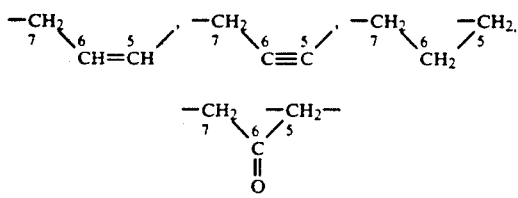

R$_1$ is hydrogen, physiologically acceptable salt thereof, physiologically acceptable protective group or C$_{1-4}$ alkyl;

R$_2$ is hydrogen or methyl;

R$_3$ is hydroxyl, methyl or hydroxymethyl;

R$_4$ and R$_5$ are same or different to represent hydrogen, methyl, hydroxyl or halogen;

R$_6$ is C$_{1-9}$ alkyl which may be branched or contain double bond, or C$_{1-9}$ alkyl which contains ether substituent wherein carbons at 2 and 3 position may be doubly bonded; except when R$_1$, R$_2$, R$_4$ and R$_5$ are hydrogens, R$_3$ is hydroxyl, R$_6$ is n-butyl, carbons at 2 and 3 positions are singly bonded, and (X) is A, C or D;

and tranquilizers and soporifics containing 13,14-dihydro-15-keto-PGDs as aforementioned.

(X) is the general formula (I) represents above four constructions.

The compound wherein —(X)— represents

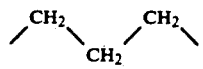

is prostaglandins D$_1$, and the compound wherein —(X)— represents

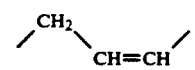

is prostaglandins D$_2$. Therefore, a compound wherein —(X)— represents

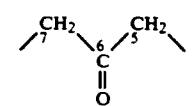

is 6-keto-PGD$_1$s, and

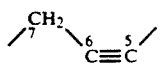

is 5,6-dehydro-PGD$_2$s.

In the present invention, R$_1$ represents hydrogen, ester residue, salt or protective group. The preferred R$_1$ in the present invention is ester residue. More preferably, it is saturated or unsaturated alkyl which may contain side chain, especially alkyl which may contain C$_{1-4}$ side chain, for example, methyl, ethyl, n-propyl, isopropyl, n-butyl, tert-butyl and the like.

Free PGDs may form salt thereof with suitable alkali. When used as a medicament, physiologically acceptable alkali may be used. Such alkali includes alkali metal, alkaline earth metal, ammonia, lower amine, alkanolamine, heterocyclic compound, for example, sodium, potassium, calcium, magnesium, methylamine, dimethylamine, cyclopentylamine, benzylamine, piperidine, monoethanolamine, diethanolamine, monomethylethanolamine, tromethamine, lysine, tetraalkylammonium salt and the like.

As a protective group there are exeplified alkylsilicon such as trimethylsilicon, triethylsilicon and the like; tetrahydroxypyran and the like.

R$_2$ is hydrogen or methyl and carbons at 2 and 3 positions may be doubly bonded.

R$_3$ is hydroxyl, methyl or hydroxymethyl, wherein configuration of the carbon at 9 position is α, β, or mixture thereof. Particularly, those with α-configuration is preferred.

R$_4$ and R$_5$ are independently represent hydrogen, methyl, hydroxyl or halogen. R$_4$ and R$_5$ may be same or different.

R$_6$ is saturated or unsaturated C$_{1-9}$ alkyl which may be branched. C$_{4-9}$ alkyl is preferred. As C$_{4-9}$ alkyl, straight alkyl or that having methyl side chain is particularly preferable.

R$_6$ is saturated or unsaturated C$_{1-9}$ alkyl having ether substituent. As alkyl group, C$_{2-6}$ alkyl, especially straight alkyl is preferred. Ether substituent includes methoxy and ethoxy. Particularly, those having substituent at the end of their alkyl chains are preferred.

Typical examples of the compounds of the present invention will be shown below:

13,14-dihydro-15-keto-PGD$_2$ alkyl ester;

13,14-dihydro-15-keto-16,16-dimethyl-PGD$_2$ and alkyl ester thereof;

13,14-dihydro-15-keto-19-methyl-PGD$_2$ and alkyl ester thereof;

13,14-dihydro-15-keto-16R,S-fluoro-PGD$_2$ and alkyl ester thereof;

13,14-dihydro-15-keto-20-methoxy-PGD$_2$ and alkyl ester thereof;

13,14-dihydro-15-keto-18-methoxy-19,20-bisnor-PGD$_2$ and alkyl ester thereof;

13,14-dihydro-15-keto-19-ethoxy-20-nor-PGD$_2$ and alkyl ester thereof;

13,14-dihydro-15-keto-20-methoxyethyl-PGD$_2$ and alkyl ester thereof;

13,14-dihydro-15-keto-20-methoxy-Δ$^2$-PGD$_2$ and alkyl ester thereof;

13,14-dihydro-15-keto-3R,S-methyl-20-methoxy-PGD$_2$ and alkyl ester thereof;

13,14-dihydro-15-keto-16R,S-methyl-20-methoxy-PGD$_2$ and alkyl ester thereof;

13,14-dihydro-15-keto-16,16-dimethyl-20-methoxy-PGD$_2$ and alkyl ester thereof;

13,14-dihydro-15-keto-19-methyl-20-methoxy-PGD$_2$ and alkyl ester thereof;

13,14-dihydro-15-keto-16R,S-fluoro-20-methoxy-PGD$_2$ and alkyl ester thereof;

13,14-dihydro-15-keto-5,6-dehydro-PGD$_2$ and alkyl ester thereof;

13,14-dihydro-15-keto-5,6-dehydro-20-methoxy-PGD$_2$ and alkyl ester thereof;

13,14-dihydro-15-keto-5,6-dehydro-$\beta$-hydroxy-PGD$_2$ and alkyl ester thereof;

13,14-dihydro-15-keto-5,6-dehydro-$\beta$-hydroxy-20-methoxy-PGD$_2$ and alkyl ester thereof;

and the like.

In order to synthesize the prostaglandins of the D series of the present invention, for example, as shown in the attached synthetic charts 1-8, commercially available corey lactone (1) is used as a starting material, which is subjected to collins oxidization to give aldehyde (2), and the resultant is reacted with dimethyl(2-oxoalkyl)-phosphonate to give $\alpha,\beta$-unsaturated ketone (3). The resulting $\alpha,\beta$-unsaturated ketone (3) is subjected to chemical or catalytic reduction, followed by conversion into ketanol, introduction of $\alpha$-chain, Jones oxidization and the like to give the objective compound.

The prostaglandins of the D series of the present invention may be used as a medicament for animals or human. Usually, they can be generally or locally administered, for example, by oral administration, intravenous injection, subcutaneous injection or the like. The dose level may vary depending on the animals, human, age, weight, conditions, therapeutic effect, route of administration, period for treatment and the like.

Solid compositions for oral administration according to the present invention include tablets, powder, glanules and the like. In such solid compositions, one or more active substances may be mixed with at least one inert diluent, for example, lactose, mannitol, glucose, hydroxypropyl cellulose, microcrystalline cellulose, starch, polyvinyl pyrrolidone, magnesium aluminate metasilicate and the like. According to the conventional manner, the composition may contain additives other than inert diluent, for example, lubricant such as magnesium stearate, disintegrants such as fibrous calcium gluconate, stabilizing agents such as etherified cyclodextrin, e.g., $\alpha$-, $\beta$- or $\gamma$-cyclo-dextrin, dimethyl-$\alpha$, dimethyl-$\beta$-, trimethyl-$\beta$- or hydroxypropyl-$\beta$-cyclodextrin, branched cyclodextrin such as glucosyl-, maltosyl-cyclodextrin, formyl-cyclodextrin, cyclodextrin containing sulfur, misoprotol, phospholipid and the like. When the above cyclodextrins are used, clathrate compound may be formed to increase stability. Alternatively, liposome is formed using phospholipids to increase stability. Tablets or pills may be optionally coated with gastric or enteric film such as sucrose, gelatin, hydroxypropylmethyl cellulose phthalate and the like. Alternatively, they may be coated with more than two layers. Further, they may be formulated as capsules using substances which can be absorbed, such as gelatin.

Liquid compositions for oral administration may contain pharmaceutically acceptable emulsion, solution, suspension, syrup, elixir, as well as generally used inert diluent such as purified water, ethanol, vegetable oil, e.g., coconut oil. Such compositions may contain adjuvant such as humectant, suspension, sweetener, flavor, preservatives in addition to inert diluent. Alternatively, such liquid compositions may be enclosed in soft capsules.

Other compositions for oral administration include sprays containing one or more active substances, which can be formulated by known methods.

Injection for parenteral administration according to the present invention includes sterile, aqueous or non-aqueous solution, suspension, emulsion, or surface active agents.

Aqueous solution and suspension include, for example, injectable distilled water and physiological saline. Non-aqueous solution and suspension include, for example, propylene glycol, polyethylene glycol, vegetable oil such as olive oil, alcohols such as ethanol, Polysorbate and the like. Such compositions may further contain adjuvants such as preservatives, humectants, emulsifying agent, dispersant and the like. They may be sterilized, for example, by filtration through bacteria-retaining filter, or by compounding bactericide or by irradiation. Alternatively, sterile solid composition is prepared, which is dissolved in sterile water or sterile solvent for injection before use.

EXAMPLE 1 (CF. SYNTHETIC CHART 1)

Synthesis of 13,14-dihydro-15-keto PGD$_2$ ethyl ester (1), R=Et (1-1) Synthesis of 1S-2-oxa-3-oxo-6R-(3-oxo-1-trans-octenyl)-7R-(4-phenylbenzoyl)oxy-cis-bicyclo (3,3,0)octane (3)

(−)-Corey lactone (1) (2.000 g) dissolved in dichloromethane (20 ml) was oxidized using collins reagent to give aldehyde (2). sodium hydride (50%, 0.264 g) was suspended in dry THF (45 ml), and after adding a solution of dimethyl (2-oxo-heptyl)phosphonate (1.475 g) in THF, stirred at room temperature for 90 minutes. A solution of aldehyde (2) in THF (40 ml) was added dropwise to the above solution and let to stand overnight at room temperature. The crude product obtained after the usual work-up was chromatographed (ethyl acetate/hexane (1:3)). Yield, 1.618 g (64%).

(1-2) Synthesis of 1S-2-oxa-3-oxo-6R-(3,3-ethylenedioxy-1-octyl)-7R-(4-phenylbenzoyl)oxy-cis-bicyclo(3,3,0)octane (5)

Saturated ketone (4) obtained after catalytic hydrogenation of enone (3) (1.618 g) with palladium on carbon and hydrogen was converted into the corresponding ketal (5) using ethylene glycol and p-toluenesulfonic acid in benzene. Yield, 0.2010 g (70%).

(1-3) Synthesis of 1S-2-oxa-3-oxo-6R-(3,3-ethylenedioxy-octyl)-7R-hydroxy-bicyclo(3,3,0)-octane (6)

Potassium carbonate (0.116 g) was added to ketal (5) (0.2010 g) in absolute methanol, and stirred at room temperature. After the reaction was completed, acetic acid was added. The crude product obtained after the usual work-up was chromatographed (ethyl acetate/hexane (1:1)) to give alcohol (6). Yield, 0.090 g (73%).

(1-4) Synthesis of 13,14-dihydro-15,15-ethylenedioxy-PGF$_{2\alpha}$(8)

Alcohol (6) (0.090 g) was reduced in toluene with diisobutylalumiumhydride (DIBAL-H 1.5-M) to give lactol (7). According to the conventional method, a solution of lactol (7) in DMSO was added to ylide obtained from (4-carboxy-butyl)triphenylphosphonium bromide (0.5406 g) in DMSO to give 13,14-dihydro-15,15-ethylenedioxy-PGF$_2$α(8). Yield, 0.0644 g (53%).

(1-5) Synthesis of 13,14-dihydro-15,15-ethylenedioxy-PGF$_2$αethyl ester (9), R=Et Carboxylic acid (8) (0.0644 g) was esterified with diazobicycloundecene (DBU) (0.024 ml) and ethyl iodide in acetonitrile (10 ml) at 60° C. to yield ethyl ester (9). Yield, 0.0594 g (86%).

(1-6) Synthesis of 13,14-dihydro-15-keto-PGF$_2$αethyl ester (10), R=Et

Ethyl ester (9) was dissolved in a mixed solvent (acetic acid/water/THF (3:1:1)) (6 ml) and kept at room temperature. The crude product obtained after the usual work-up was chromatographed (ethyl acetate/hexane (1:1)) to give 13,14-dihydro-15-keto-PGF$_2$α ethyl ester (10). Yield, 0.0457 g (86%).

(1-7) Synthesis of 13,14-dihydro-15-keto-PGD$_2$ ethyl ester (11), R=Et

Ethyl ester (10) (0.0457 g) was oxidized with Jones reagent in acetone (10 ml). After the usual work-up, the resulting crude product was chromatographed (ethyl acetate/hexane (1:3)). Yield, 0.0260 g (57%)).

Nmr spectrum of 13,14-dihydro-15-keto-PGD$_2$ ethyl ester (11) is shown in FIG. 1.

EXAMPLE 2 (CF. SYNTHETIC CHART 1)

Synthesis of 13,14-dihydro-15-keto-PGD$_2$ (11), R=H

Carboxylic acid (8) was deketalized according to the usual method to give 13,14-dihydro-15-keto-PGF$_2$α (10). The resultant (10) was oxidized with Jones reagent to give 13,14-dihydro-15-keto-PGD$_2$ (11), R=H.

EXAMPLE 3 (CF. SYNTHETIC CHART 1)

Synthesis of 13,14-dihydro-15-keto-PGD$_2$ methyl ester (11), R=Me 13,14-Dihydro-15-keto-PGD$_2$ (11), R=H, was converted into methyl ester using diazo-methane. After chromatography (ethyl acetate/hexane(1:3)), 13,14-dihydro-15-keto-PGD$_2$ methyl ester (11), R=Me, was obtained. Yield, 0.0610 g (50%).

Carboxylic acid (8) was converted into methyl ester (9), R=Me, with DBU and methyl iodide in acetonitrile, then into 13,14-dihydro-15-keto-PGD$_2$ methyl ester (11), R=Me.

Figure 2:
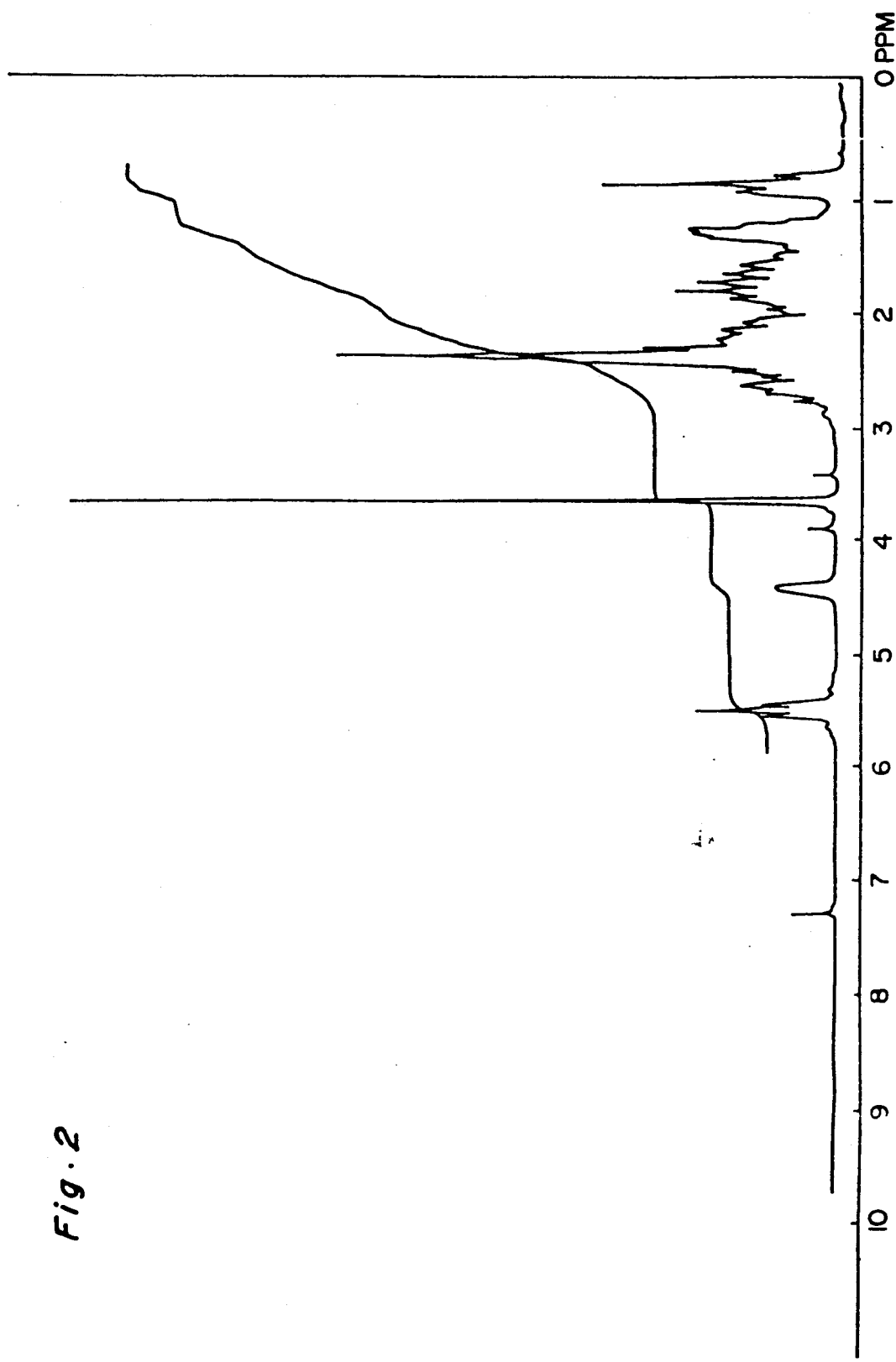

NMR spectrum of 13,14-dihydro-15-keto-PGD$_2$ methyl ester (11), R=Me, is shown in FIG. 2.

EXAMPLE 4 (CF. SYNTHETIC CHART 1)

Synthesis of 13,14-dihydro-15-keto-PGD$_2$ n-butyl ester (11), R=n-Bu

In the manner analogous to that described in Example I, except that carboxylic acid (8) obtained from (−)-Corey lactone (1) was converted into n-butyl ester (9), R=n-Bu, with n-butyl bromide and DBU in acetonitrile, 13,14-dihydro-15-keto-PGD$_2$ n-butyl ester (11), R=n-Bu, was obtained.

Figure 3:
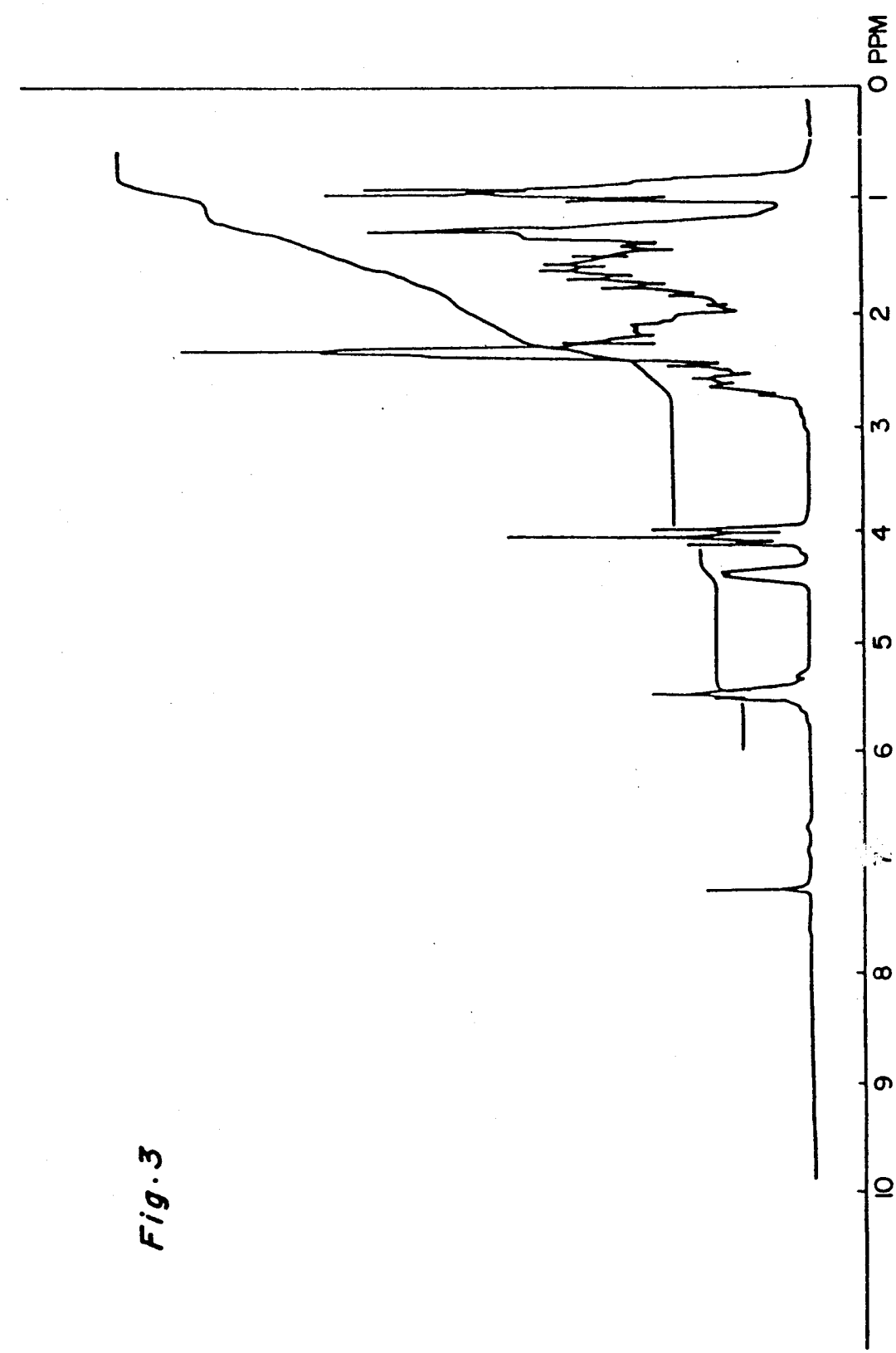

NMR spectrum of 13,14-dihydro-15-keto-PGD$_2$ n-butyl ester (11), R=n-Bu, is shown in FIG. 3.

EXAMPLE 5 (CF. SYNTHETIC CHART 2)

Synthesis of 13,14-dihydro-15-keto-20-methoxy-PGD$_2$ methyl ester (20), R=Me

In the same manner as in Example 1, 13,14-dihydro-15-keto-20-methoxy-PGD$_2$ methyl ester (20) was synthesized using (−)-Corey lactone (1) and dimethyl (7-methoxy-2-oxoheptyl)phosphonate prepared by the conventional method. To produce methyl ester of carboxylic acid (17), diazomethane or methyl iodide and DBU can be use.

Figure 4:
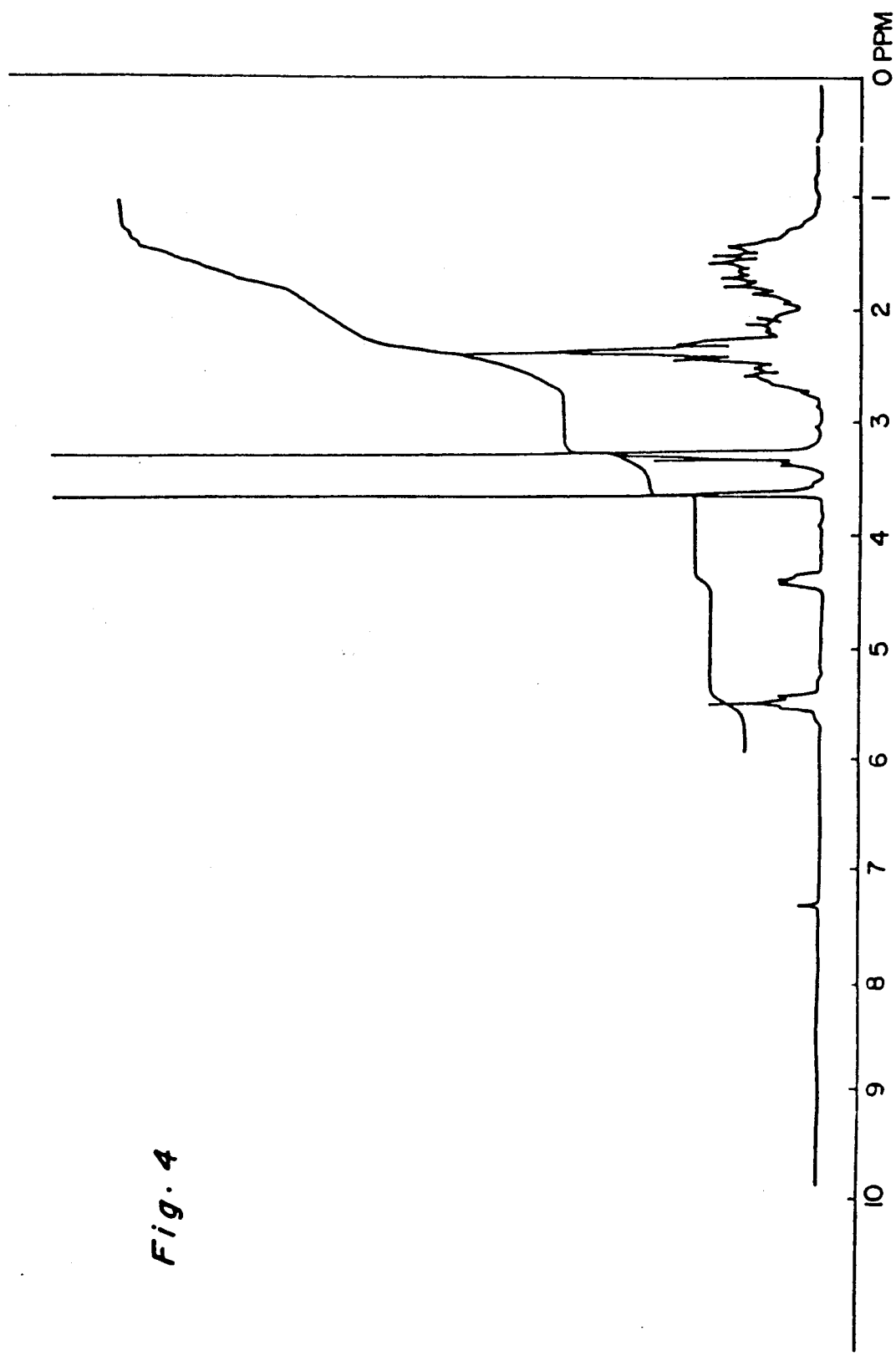

NMR spectrum of 13,14-dihydro-15-keto-20-methoxy-PGD$_2$ methyl ester (20), R=Me, is shown in FIG. 4.

EXAMPLE 6 (CF. SYNTHETIC CHART 3)

Synthesis of 13,14-dihydro-15-keto-20-methoxy-PGD$_2$ (31)

(6-1) Synthesis of 1S-2-oxa-3-oxo-6R-(3R,S-hydroxy-8-methoxy-1-octyl)-7R-(p-phenylbenzoyl)oxy-cis-bicyclo(3,3,0)octane (21)

1S-2-Oxa-3-oxo-6R-(8-methyoxy-3-oxo-octyl)-7R-(p-phenylbenzoyl)oxy-cis-bicyclo(3,3,0)-octane (13) (1.584 g) was reduced with NaBH$_4$ in a mixed solvent (methanol/THF (3:2)) (50 ml), then chromatographed (ethyl acetate/hexane (2:1)) to give alcohol (21). Yield, 0.7070 g.

(6-2) Synthesis of 1S-2-oxa-3-oxo-6R-(3R,S-hydroxy-8-methoxy-1-octyl)-7R-hydroxy-cis-bicyclo-(3,3,0)octane (22)

1S-2-Oxa-3-oxo-6R-(3R,S-hydroxy-8-methoxy-1-octyl)-7R-(p-phenylbenzoyl)oxy-cis-bicyclo-(3,3,0)octane (21) (0.7070 g) was dissolved in a mixed solvent of methanol/THF (3:2) (50 ml), potassium carbonate (0.2034 g) was added thereto and stirred for 4 hours. According to the conventional treatment, diol (22) was obtained. Yield, 0.3925 g.

(6-3) Synthesis of 1S-2-oxa-3-oxo-6R-(3R,S-t-butyldimethylsilyloxy-8-methoxy-1-octyl)-7R-t-butyldimethylsilyloxy-cis-bicyclo(3,3,0)octane (23)

Diol (22) (0.3925 g) was converted into the corresponding silyl ether (23) using t-butyldimethylsilyl chloride (0.5928 g) and dimethylaminopyridine (0.640 g) in dichloromethane. Yield, 0.3642 g.

(6-4) Synthesis of 13,14-dihydro-11,15R,S-di(t-butyldimethylsilyloxy)-20-methoxy-PGF$_2$αmethyl ester (26)

Silyl ether (23) (0.3642 g) was reduced with DIBALH (1.5-M, 1.4 ml) in toluene (20 ml), and according to the conventional treatment, lactol (24) was obtained. Separately, ylide was prepared from (4-carboxybutyl)triphenylphosphonium bromide (1.223 g) and potassium butoxide (0.6194 g) in THF (180 ml), to which was added the above lactol. After the reaction was completed, carboxylic acid (25) was obtained by the conventional treatment. The resultant was treated with diazomethane to give methyl ester (26). Yield, 0.176 g.

(6-5) Conversion of the compound (26) into tetrahydro pyranyl ether

The above methyl ester (26) (0.176 g) was converted into tetrahydropyranyl ether (27) with p-toluenesulfonic acid (catalytic amount) and dihydropyran in dichloromethane (10 ml). Yield, 0.222 g.

(6-6) Synthesis of 13,14-dihydro-15R,S-hydroxy-20-methoxy-9-(2-tetrahydropyranyl)oxy-PGF$_2\alpha$(29)

Methyl ester (27) (0.2220 g) was dissolved in THF (10 ml), to which was added tetrabutylammonium fluoride (1-M, 1.91 ml), and allowed to stand at room temperature. According to the conventional treatment, diol (28) was obtained. Yield, 0.816 g.

The diol (28) (0.816 g) was dissolved in methanol (10 ml), to which was added 20% sodium hydroxide (5 ml) and held at room temperature for 2 hours. According to the conventional treatment, carboxylic acid (29) was obtained.

(6-7) Synthesis of 13,14-dihydro-15-keto-20-methoxy-PGD$_2$ (31)

Carboxylic acid (29) was oxidized with Jones reagent in actone (10 ml) at −37° C. (2.6-M, 0.15 ml). 13,14-Dihydro-15-keto-20-methoxy-9-(2-tetrahydropyranyl)oxy-PGD$_2$ (30) was obtained according to the conventional treatment. The resulting compound (30) was dissolved in a mixed solvent (acetic acid/water/THF (4:2:1)) (7 ml) and held at 40°–43° C. for 3 hours. After the conventional treatment, the compound was chromatographed (ethyl acetate/hexane (4:1)) to give 13,14-dihydro-15-keto-20-methoxy-PGD$_2$(31). Yield, 0.059 g.

Figure 5:
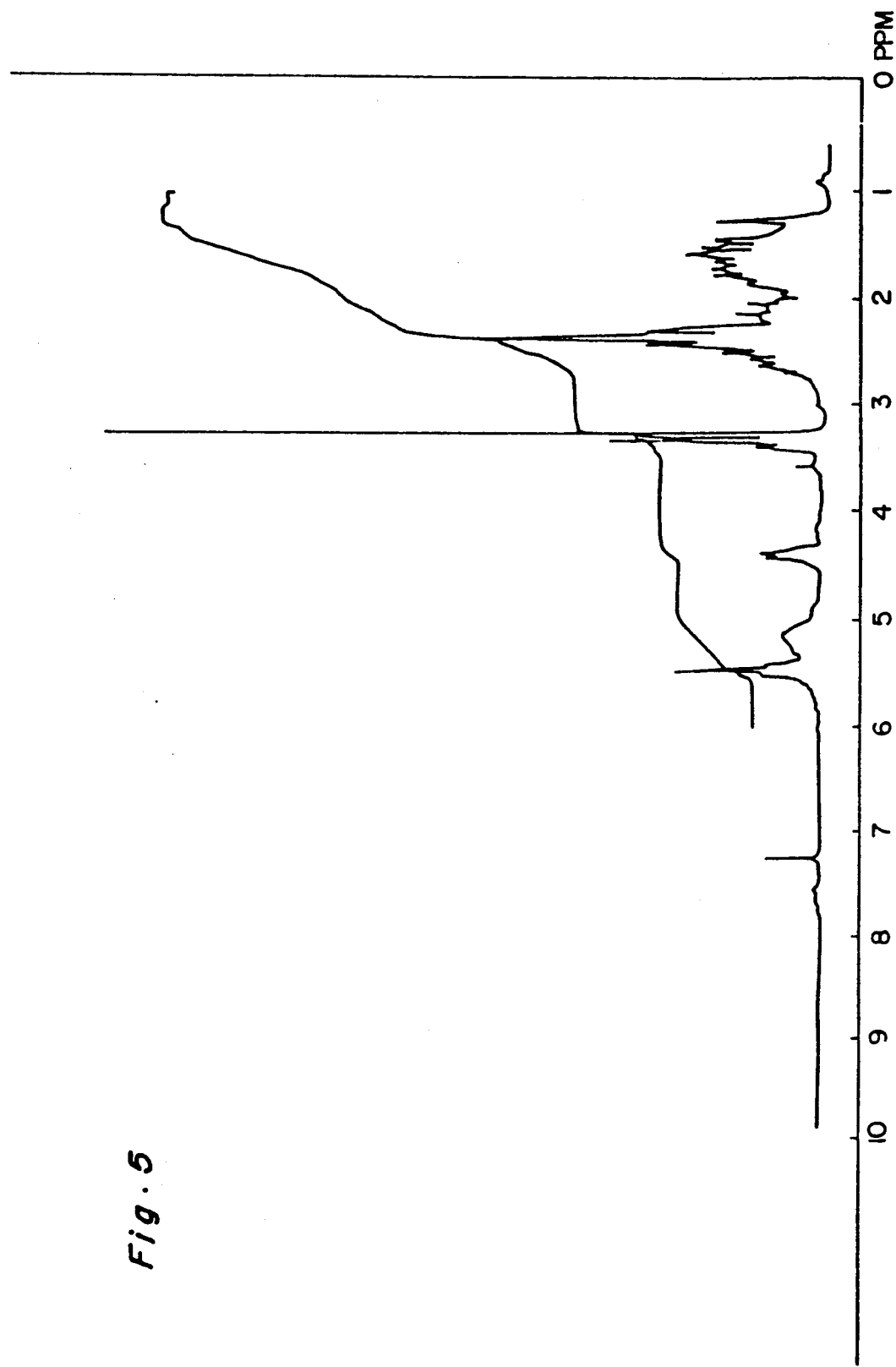

NMR spectrum of 13,14-dihydro-15-keto-20-methoxy-PGD$_2$ (31) is shown in FIG. 5.

EXAMPLE 7 (CF. SYNTHETIC CHART 2)

Synthesis of 13,14-dihydro-15-keto-3R,S-methyl-20-methoxy-PGD$_2$ methyl ester (32)

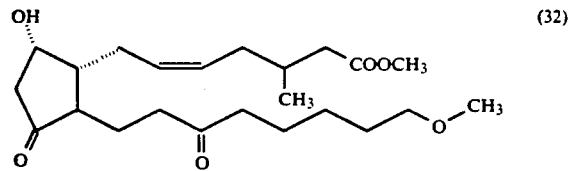

In the same manner as in Example 5, 13,14-dihydro-15-keto-3R,S-methyl-20-methoxy-PGD$_2$ methyl ester (32) was synthesized using (−)-Corey lactone (1) and dimethyl(7-methoxy-2-oxo-heptyl)phosphonate prepared by the known method.

Figure 6:
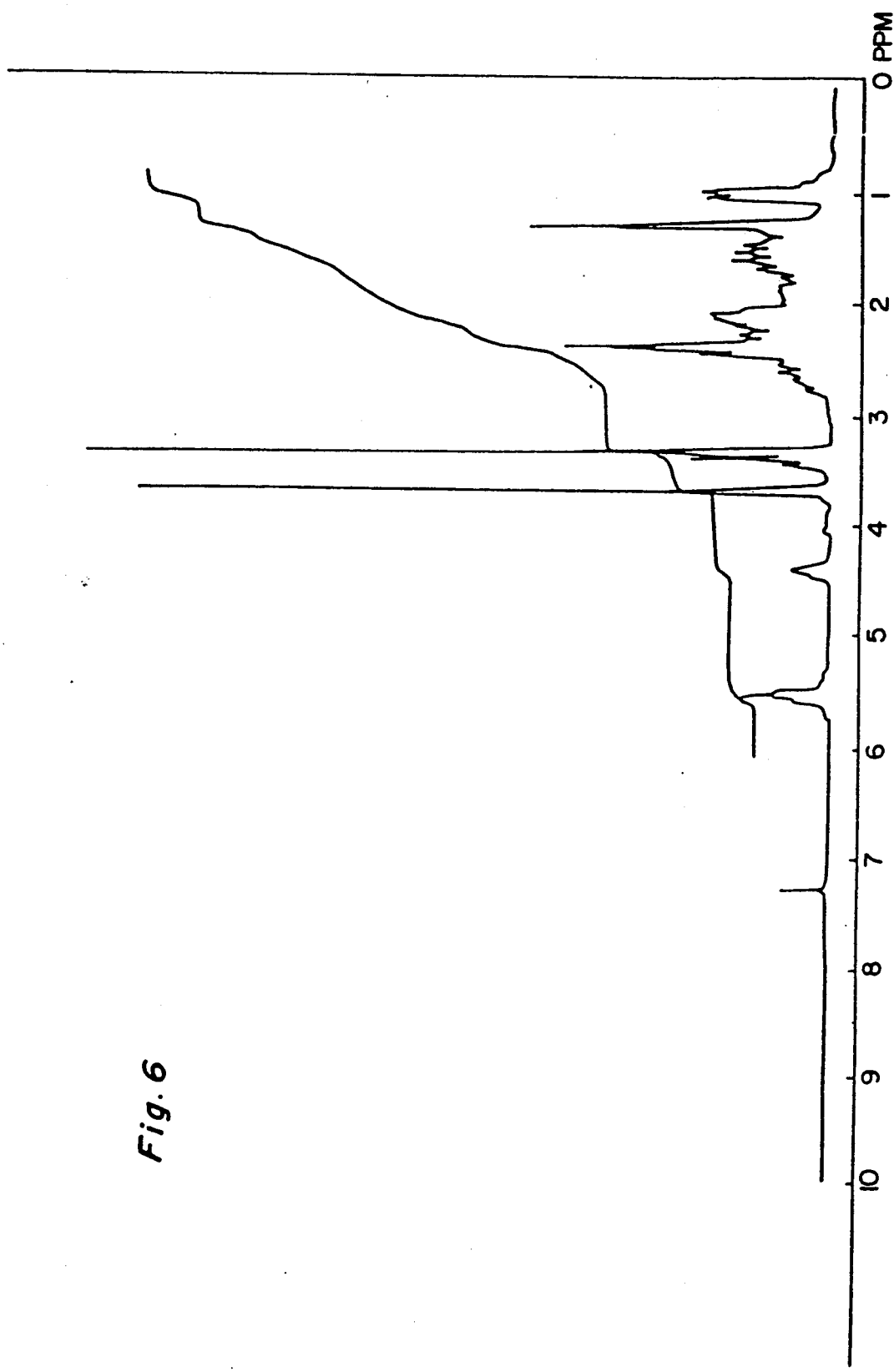

NMR spectrum of 13,14-dihydro-15-keto-3R,S-methyl-20-methoxy-PGD$_2$ methyl ester (32) is shown in FIG. 6.

EXAMPLE 8 (CF. SYNTHETIC CHART 2)

Synthesis of 13,14-dihydro-15-keto-20-methoxyethyl-PGD$_2$ methyl ester (33)

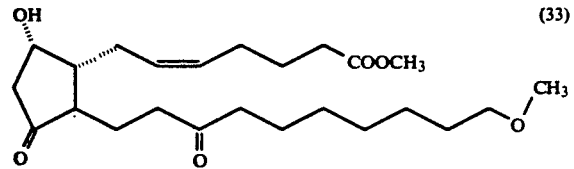

In the same manner as in Example 5, 13,14-dihydro-15-keto-20-methoxyethyl-PGD$_2$ methyl ester (33) was synthesized using (−)-Corey lactone (1) and dimethyl(7-methoxy-2-oxononyl)phosphonate prepared by the known method.

Figure 7:
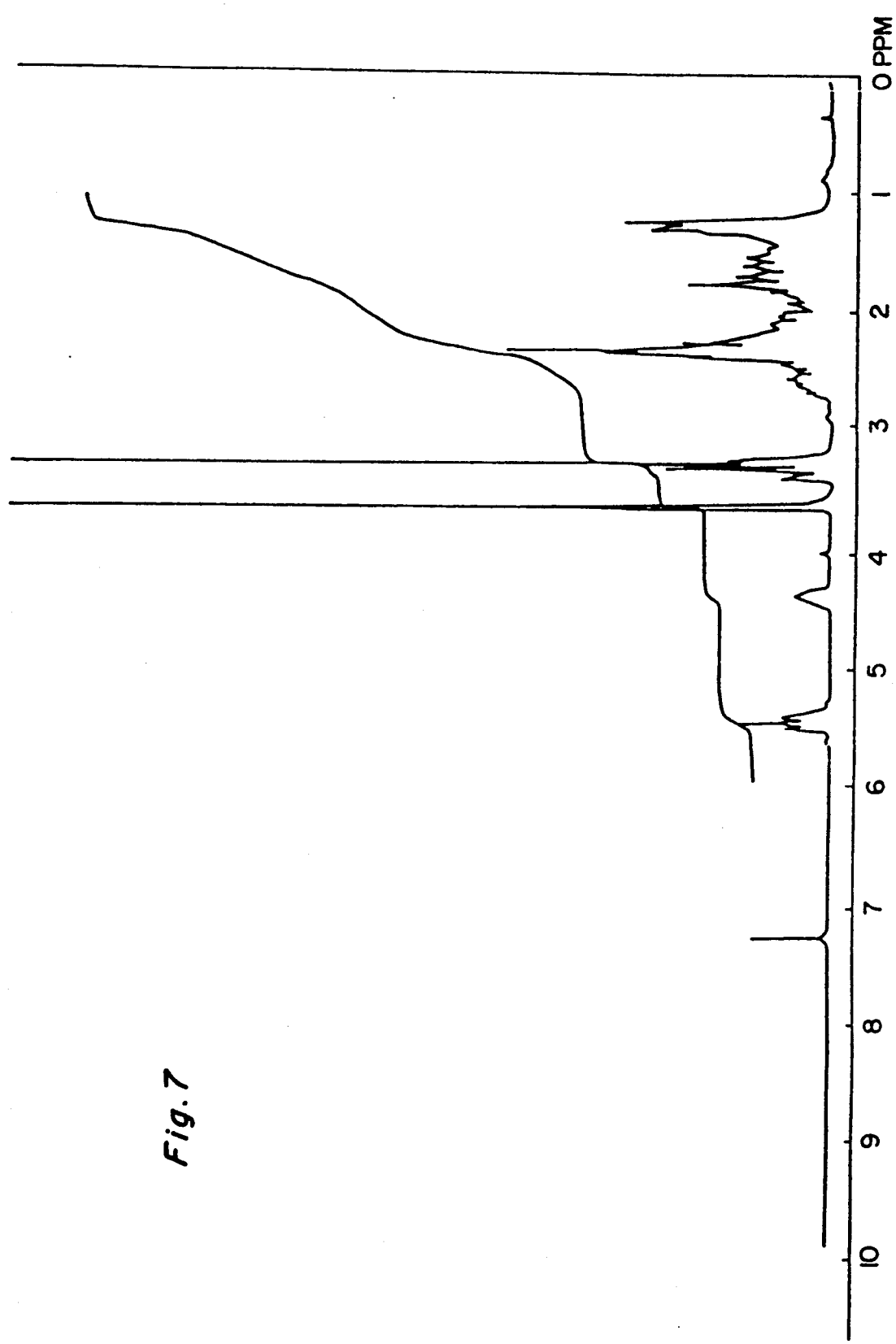

NMR spectrum of 13,14-dihydro-15-keto-20-methoxyethyl-PGD$_2$ methyl ester (33) is shown in FIG. 7.

EXAMPLE 9 (CF. SYNTHETIC CHARTS 2 AND 4)

Synthesis of 13,14-dihydro-15-keto-20-methoxy-$\Delta^2$-PGD$_2$ methyl ester (38)

(9-1) Synthesis of 13,14-dihydro-15,15-ethylenedioxy-20-methoxy-9,11-di(t-butyldimethylsilyloxy)-PGF$_2\alpha$ methyl ester (34)

13,14-Dihydro-15,15-ethylenedioxy-20-methoxy-PGF$_2\alpha$ methyl ester (18) (0.5472 g) was converted into 13,14-dihydro-15,15-ethylenedioxy-20-methoxy-9,11-di(t-butyldimethylsilyloxy)PGF$_2\alpha$ methyl ester (34) using t-butyldimethylsilyl chloride (0.9428 g) and imidazole (0.8519 g) in DMF (10 ml). Yield, 0.8015 g.

(9-2) Synthesis of 13,14-dihydro-15,15-ethylenedioxy-20-methoxy-9,11-di(t-butyldimethylsilyloxy)-$\Delta^2$-PGF$_2\alpha$ methyl ester (36)

Lithium cyclohexylisopropylamide was prepared from cyclohexylisopropylamine (0.07 ml) and n-butyllithium (1.6-M, 0.265 ml) in THF (1 ml). To the resultant was added dropwise a solution of methyl ester (34) (0.1412 g) in THF (4 ml) and stirred for 2 hours. A solution of diphenyl diselenide (0.132 g) and HMPA (0.074 ml) in THF (2 ml) was added, and the mixture was stirred at −70° C. for one hour and −40° C.−−30° C. for 1.5 hours. According to the conventional treatment, selenide (35) (0.1247 g) was obtained. Selenide (35) (0.1247 g) was dissolved in ethyl acetate (6 ml) and methanol (4 ml), and stirred at room temperature with aqueous hydrogen peroxide (30%) (0.5 ml) for one hour. The crude product obtained by the conventional treatment was chromatographed (ethyl acetate/hexane (1:6)) to give $\Delta^2$-PGE$_2\alpha$-methyl ester (36). Yield, 0.091 g.

(9-3) Synthesis of 13,14-dihydro-15-keto-20-methoxy-$\Delta^2$-PGF$_2\alpha$ methyl ester (37)

$\Delta^2$-PGF$_2\alpha$ methyl ester (36) (0.5458 g) was dissolved in a mixed solvent (acetic acid/water/THF (10:3.3:1)) (20 ml) and the resulting solution was held at 55° C. for 3.5 hours. By the conventional treatment, 13,14-dihydro-15-keto-20-methoxy-$\Delta^2$-PGF$_2\alpha$ methyl ester (37) was obtained. Yield, 0.2935 g.

(9-4) Synthesis of 13,14-dihydro-15-keto-20-methoxy-$\Delta^2$-PGD$_2$ methyl ester (38)

13,14-Dihydro-15-keto-20-methoxy-$\Delta^2$-PGF$_2$ $\alpha$ methyl ester (37) (0.3277 g) was oxidized with Jones reagent in acetone (20 ml) at −40° C. (2.67-M, 0.25 ml). After the conventional treatment, the resulting crude product was chromatographed (ethyl acetate/hexane (6:4)) to give 13,14-dihydro-15-keto-20-methoxy-$\Delta^2$-PGD$_2$ methyl ester (38). Yield, 0.204 g.

Figure 8:
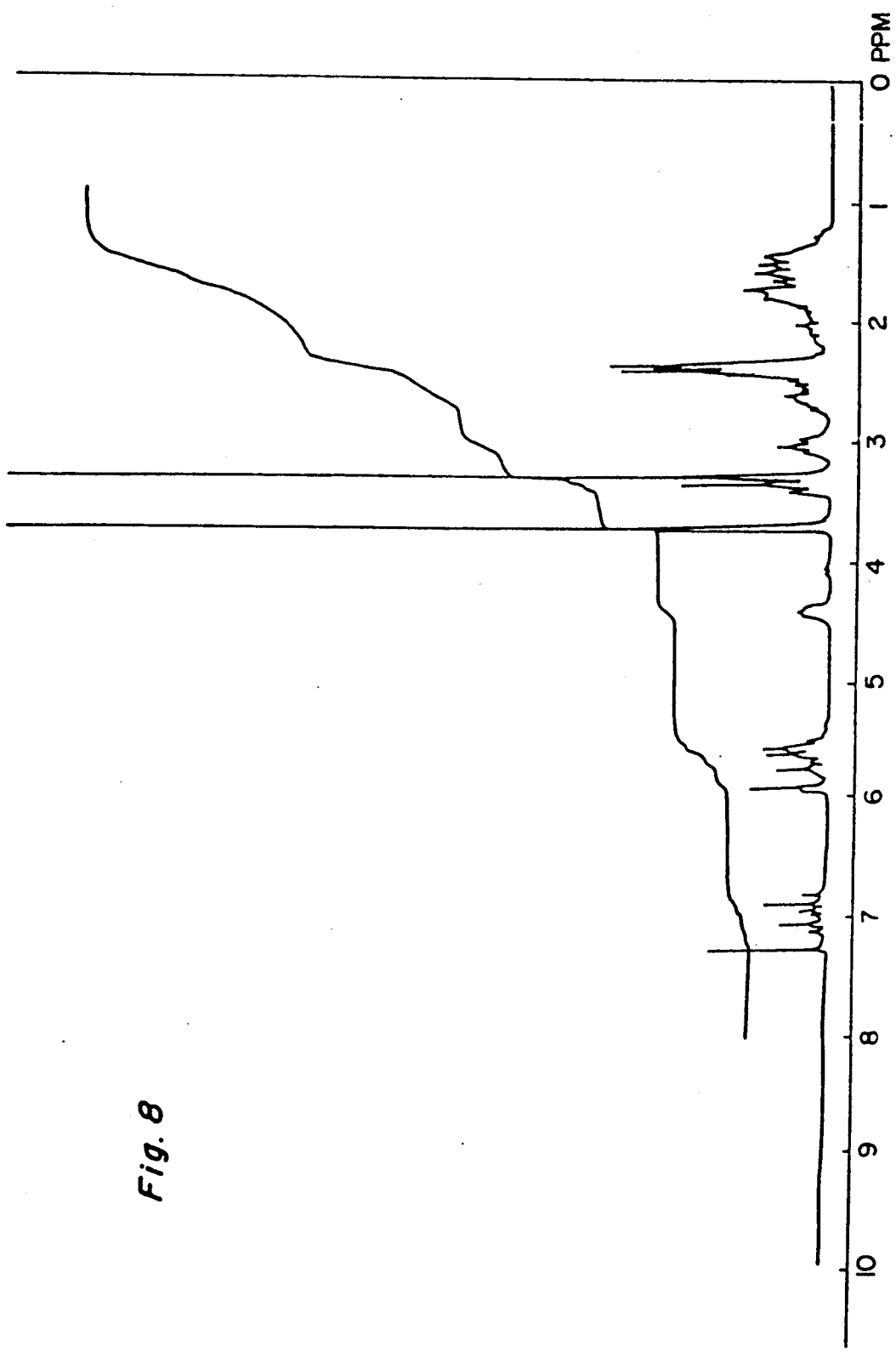

NMR spectrum of 13,14-dihydro-15-keto-20-methoxy-$\Delta^2$-PGD$_2$ methyl ester (38) is shown in FIG. 8.

EXAMPLE 10

Synthesis of 13,14-dihydro-15-keto-18-methoxy-19,20-bisnor-PGD$_2$ methyl ester (39)

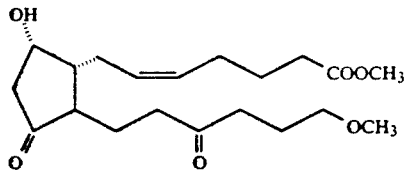
(39)

13,14-Dihydro-15-keto-18-methoxy-19,20-bisnor-PGD$_2$ methyl ester (39) was obtained in the same manner as in Example 5 using (−)-Corey lactone (1) and dimethyl(5-methoxy-2-oxopentyl)phosphonate.

Figure 9:
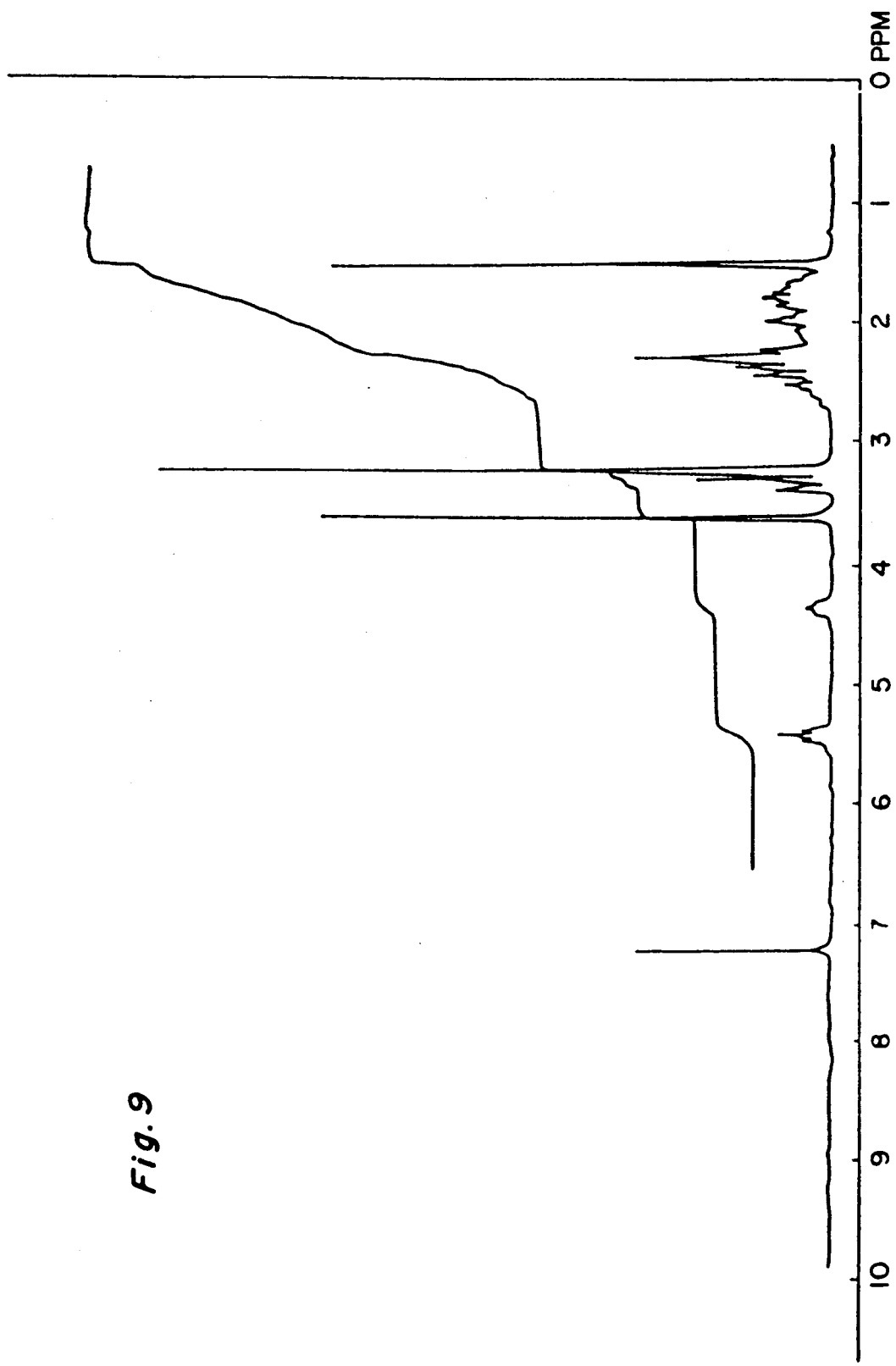

NMR spectrum of 13,14-dihydro-15-keto-18-methoxy-19,20-bisnor-PGD$_2$ methyl ester (39) is shown in FIG. 9.

EXAMPLE 11 (CF. SYNTHETIC CHART 2)

Synthesis of 13,14-dihydro-15-keto-20-methoxy-PGD$_2$ ethyl ester (20), R=Et

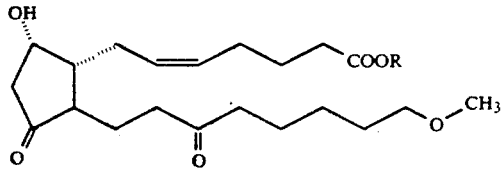
(20)

In the same manner as in Example 5, except that 13,14-dihydro-15,15-ethylenedioxy-20-methoxy-PGF$_2\alpha$(17) was converted into ethyl ester (18) with ethyl iodide and DBU in acetonitrile, 13,14-dihydro-15-keto-20-methoxy-PGD$_2$ ethyl ester (20) was prepared.

Figure 10:
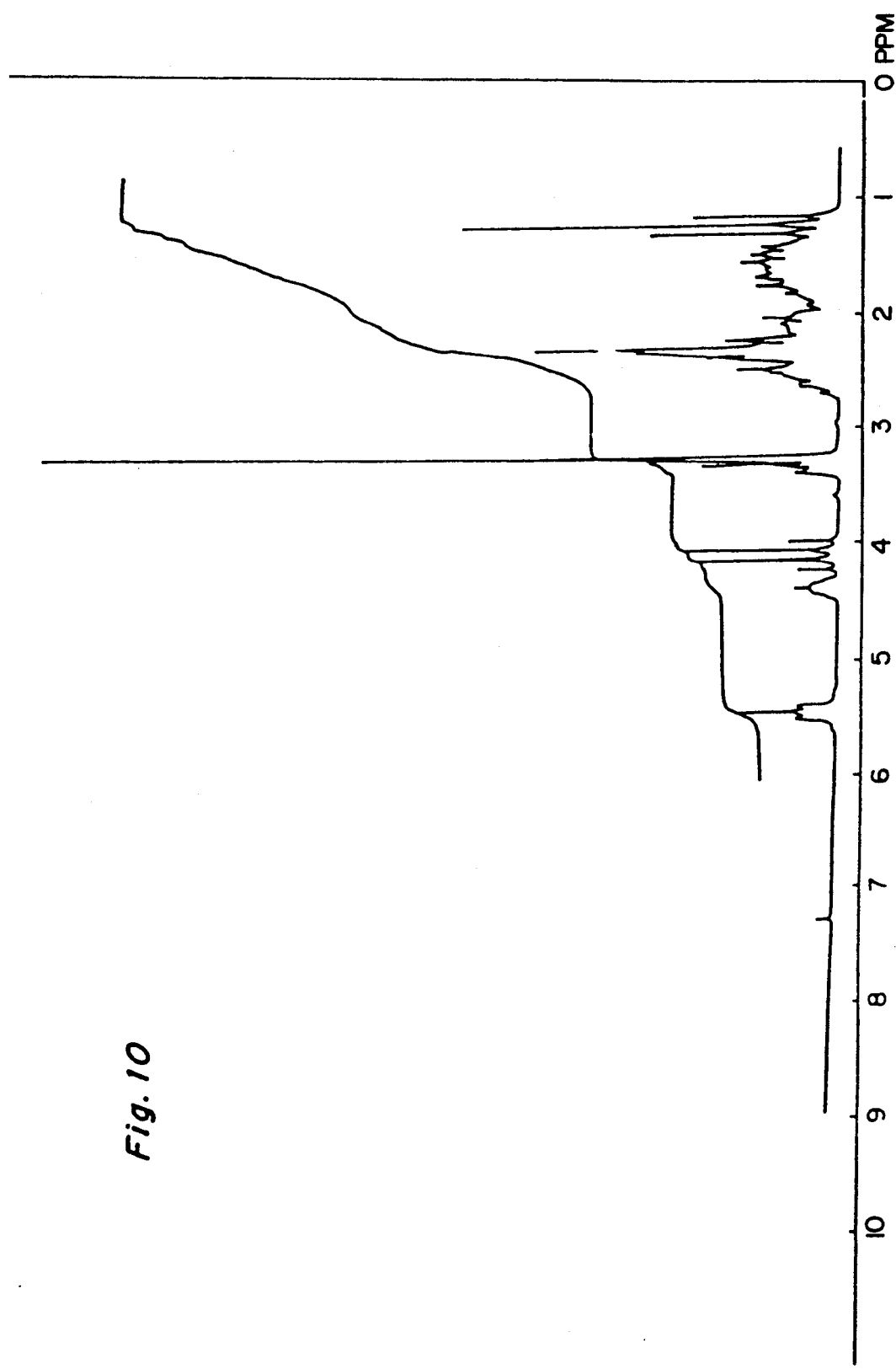

NMR spectrum of 13,14-dihydro-15-keto-20-methoxy-PGD$_2$ ethyl ester (20), R=Et, is shown in FIG. 10.

EXAMPLE 12 (CF. SYNTHETHIC CHART 2)

Synthesis of 13,14-dihydro-15-keto-20-methoxy-PGD$_2$ n-butyl ester (20), R=n-Bu In the same manner as in Example 5, except that 13,14-dihydro-15,15-ethylenedioxy-20-methoxy-PGF$_2\alpha$(17) was converted into n-butyl ester (18) with n-butyl iodide and DBU in acetonitrile, 13,14-dihydro-15-keto-20-methoxy-PGD$_2$ n-butyl ester (20), R=n-Bu, was prepared.

Figure 11:
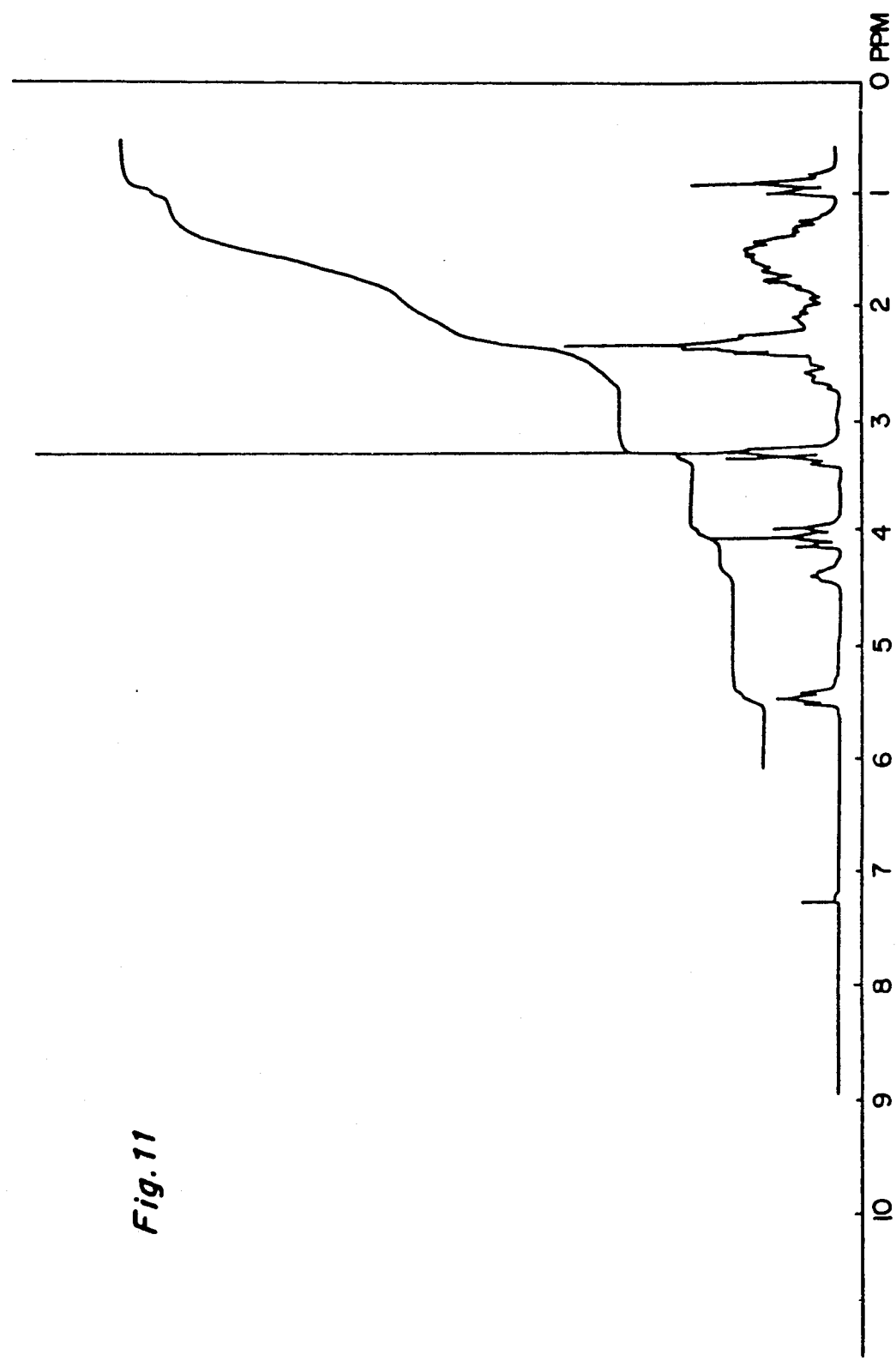

NMR spectrum of 13,14-dihydro-15-keto-20-methoxy-PGD$_2$ n-butyl ester (20), R=n-Bu, is shown in FIG. 11.

EXAMPLE 13

Synthesis of 13,14-dihydro-15-keto-16R,S-methyl-20-methoxy-PGD$_2$ methyl ester (40)

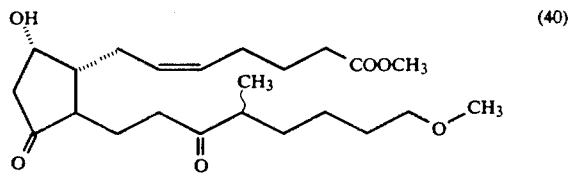
(40)

13,14-Dihydro-15-keto-16R,S-methyl-20-methoxy-PGD$_2$ methyl ester (40) was prepared in the same manner as in Example 5 using (−)-Corey lactone (1) and dimethyl(3-methyl-20-methoxy-2-oxoheptyl)phosphonate obtained by the known method.

Figure 12:
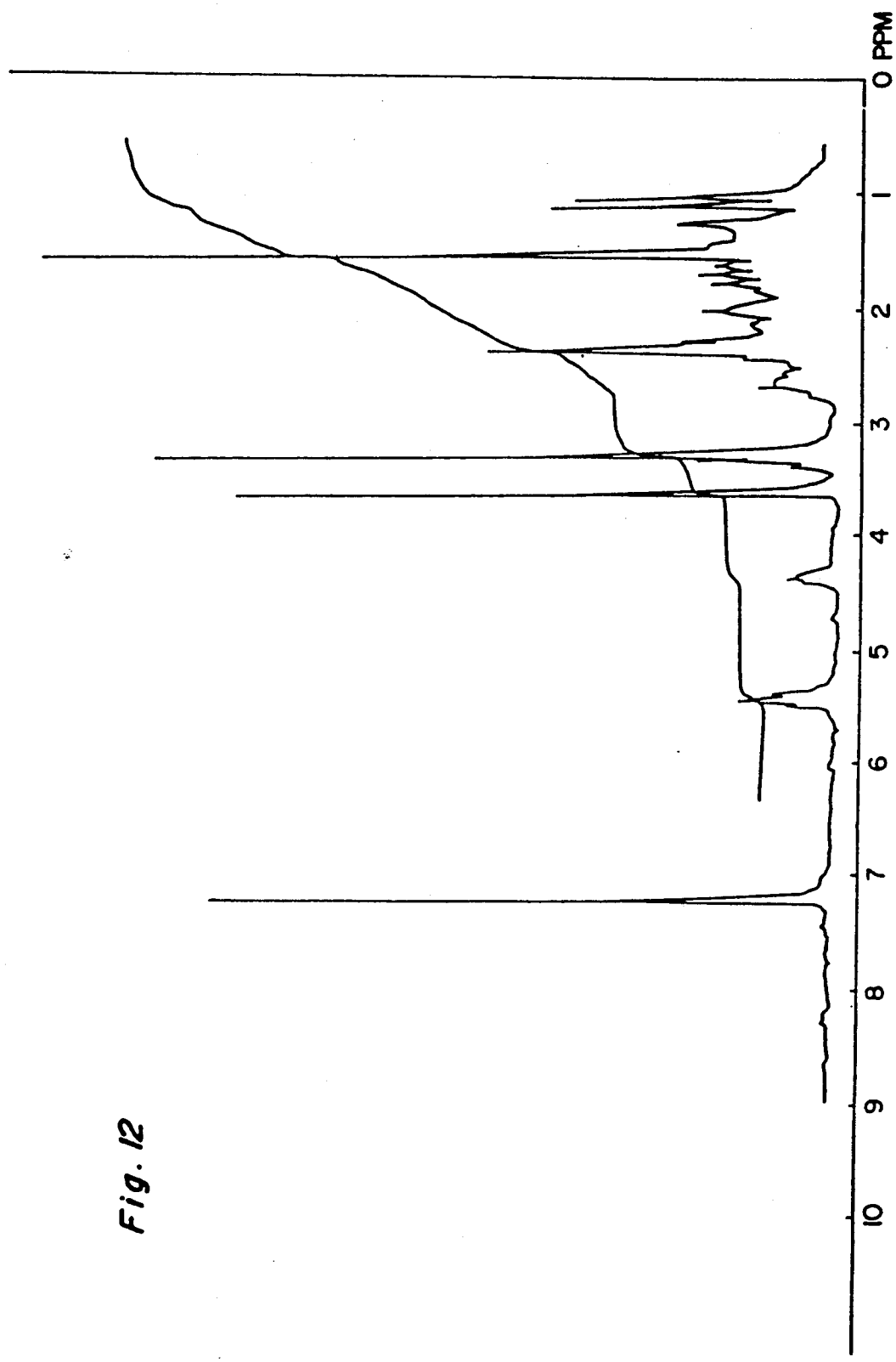

NMR spectrum of 13,14-dihydro-15-keto-16R,S-methyl-20-methoxy-PGD$_2$ methyl ester (40) is shown in FIG. 12.

EXAMPLE 14 (CF. SYNTHETIC CHART 2)

Synthesis of 13,14-dihydro-15-keto-19-ethoxy-20-nor-PGD$_2$ methyl ester (41)

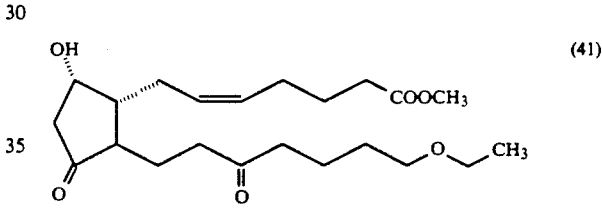
(41)

13,14-Dihydro-15-keto-19-ethoxy-20-nor-PGD$_2$ methyl ester (41) was prepared in the same manner as in Example 5 using (−)-Corey lactone (1) and dimethyl(6-ethoxy-2-oxohexyl)phosphonate obtained by the known method.

Figure 13:
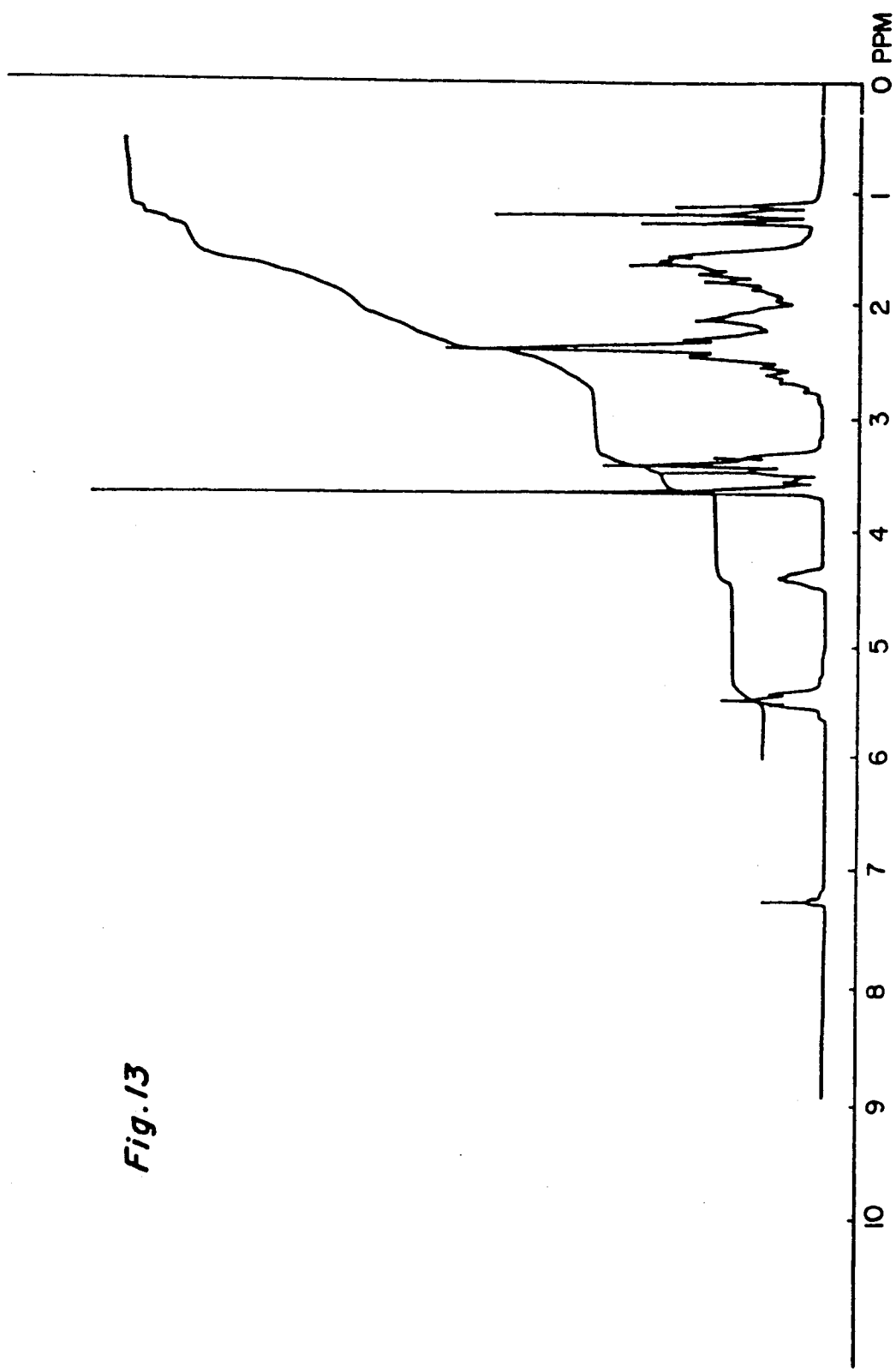

NMR spectrum of 13,14-dihydro-15-keto-19-ethoxy-20-nor-PGD$_2$ methyl ester (41) is shown in FIG. 13.

EXAMPLE 15 (CF. SYNTHETIC CHART 2)

Synthesis of 13,14-dihydro-15-keto-19-ethoxy-20-nor-PGD$_2$ n-butyl ester (42).

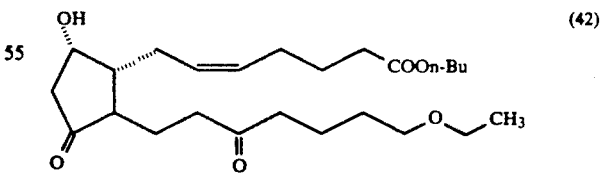
(42)

13,14-Dihydro-15-keto-19-ethoxy-20-nor-PGD$_2$ n-butyl ester (42) was prepared in the same manner as in Example 5 using (−)-Corey lactone (1) and dimethyl(6-ethoxy-2-oxohexyl)phosphonate obtained by the known method.

Figure 14:
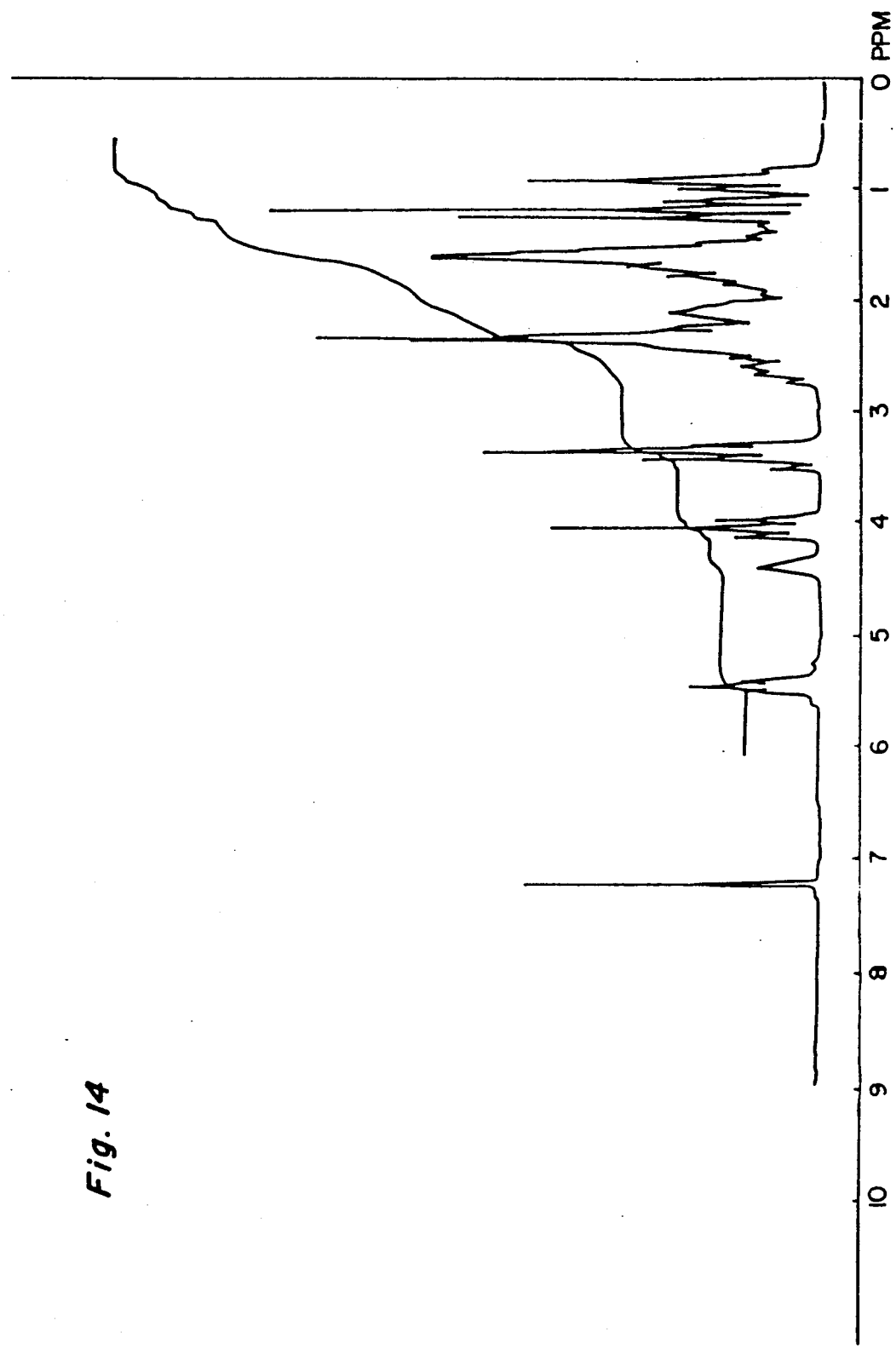

NMR spectrum of 13,14-dihydro-15-keto-19-ethoxy-20-nor-PGD$_2$ n-butyl ester (42) is shown in FIG. 14.

EXAMPLE 16 (CF. SYNTHETIC CHART 5)

Synthesis of (±)
13,14-dihydro-15-keto-5,6-dehydro-PGD$_2$ methyl ester (50)

(16-1) Synthesis of (±) 13,14-dihydro-5,6-dehydro-11,15R,S-bis(t-butyldimethylsilyl)oxy-PGE$_2$ methyl ester (44).

(±) 1-Iodo-3-(2-tetrahydropyranyl)oxy-1-octene (1.852 g) was converted into vinyllithium with t-butyllithium (in pentane, 1.92-M, 5.8 ml) in ether (25 ml) at −78° C. Separately, copper iodide (0.9522 g) was suspended in THF (25 ml), to which was added tri-n-butylphosphine (3.24 ml), and the mixture was homogenized and the temperature was brought to −78° C. The previously prepared vinyllithium solution was added to the resultant and stirred at −78° C. for 15 minutes. To the resultant was added dropwise a solution of (±) 4-t-butyldimethylsilyloxy-2-cyclopentenone (43) (1.012 g) in THF (25 ml). After adding HMPA (4.62 ml) dropwise, a solution of triphenylstannane chloride (2.029 g) in THF (10 ml) was added. After stirring at −78° C. for 30 minutes, the temperature was allowed to rise to −35° C. A solution of 1-iodo-6-carbomethoxy-2-hexyne (5.321 g) in HMPA (4.62 ml) was added dropwise to the mixture, and the resultant was stirred at −40° C. - −30° C. for 35 hours, then let to stand at −20° C. for 11.5 hours. The crude product obtained after the conventional treatment was chromatographed (ethyl acetate/hexane (1:5)) to give (±) 13,14-dihydro-5,6-dehydro-11,15R,S-bis-(t-butyldimethylsilyl)oxy-PGE$_2$ methyl ester (44) (1.510 g).

(16-2) Synthesis of (±) 13,14-dihydro-5,6-dehydro-11,15R,S-bis-(t-butyldimethylsilyl)oxy-PGF$_{2\alpha}$ methyl ester (45).

(±) 13,14-Dihydro-5,6-dehydro-11,15R,S-bis-(t-butyldimethylsilyl)oxy-PGE$_2$ methyl ester (44) (1.510 g) was reduced with sodium borohydride (NaBH$_4$) at −12° C. in ethanol to give (±) 13,14-dihydro-5,6-dehydro-11,15R,S-bis-(t-butyldimethylsilyl)oxy-PGF$_{2\alpha}$ methyl ester (45). Yield, 0.9842 g.

In this case, 9β-isomer (46) (0.2385 g) was obtained as a by-product.

(16-3) Synthesis of (±) 13,14-dihydro-5,6-dehydro-11,15R,S-bis-(t-butyldimethylsilyl)oxy-9-(2-tetrahydropyranyl)oxy-PGF$_{2\alpha}$ methyl ester (47).

(±) 13,14-Dihydro-5,6-dehydro-11,15R,S-bis-(t-butyldimethylsilyl)oxy-PGF$_{2\alpha}$ methyl ester (45) (0.9842 g) was converted into (±) 13,14-dihydro-5,6-dehydro-11,15R,S-bis-(t-butyldimethylsilyl)oxy-9-(2-tetranydropyranyl)oxy-PGF$_{2\alpha}$ methyl ester (47) with dihydropyran and p-toluenesulfonic acid in dichloromethane (20 ml). Yield, 0.7580 g.

(16-4) Synthesis of (±) 13,14-dihydro-5,6-dehydro-11,15R,S-dihydroxy-9-(tetrahydropyranyl)oxy-PGF$_{2\alpha}$ methyl ester (48).

(±) 13,14-Dihydro-5,6-dehydro-11,15R,S-bis-(t-butyldimethylsilyl)oxy-9-(2-tetrahydropyranyl)-oxy-PGF$_{2\alpha}$ methyl ester (47) (0.4484 g) was converted to diol (48) using tetrabutylammonium fluoride (1-M, 1.3 ml) in THF (50 ml). Yield, 0.2174 g.

(16-5) Synthesis of 13,14-dihydro-15-keto-5,6-dehydro-9-(2-tetrahydropyranyl)oxy-PGD$_2$ methyl ester (49).

Diol (48) (0.2174 g) was oxidized with Jones reagent (2.67M, 0.05 ml) in acetone (10 ml) to give 13,14-dihydro-15-keto-5,6-dehydro-9-(2-tetrahydropyranyl)oxy-PGD$_2$ methyl ester (49). Yield, 0.103 g.

(16-6) Synthesis of 13,14-dihydro-15-keto-5,6-dehydro-PGD$_2$ methyl ester (50).

13,14-Dihydro-15-keto-5,6-dehydro-9-(2-tetrahydropyranyl)oxy-PGD$_2$ methyl ester (49) (0.103 g) was dissolved in a mixed solvent (acetic acid/THF/water (3:1:1)) (50 ml) and held at room temperature overnight. After the conventional treatment, the crude product was chromatographed to give (±) 13,14-dihydro-15-keto-5,6-dehydro-PGD$_2$ methyl ester (50). Yield, 0.0498 g.

Figure 16:
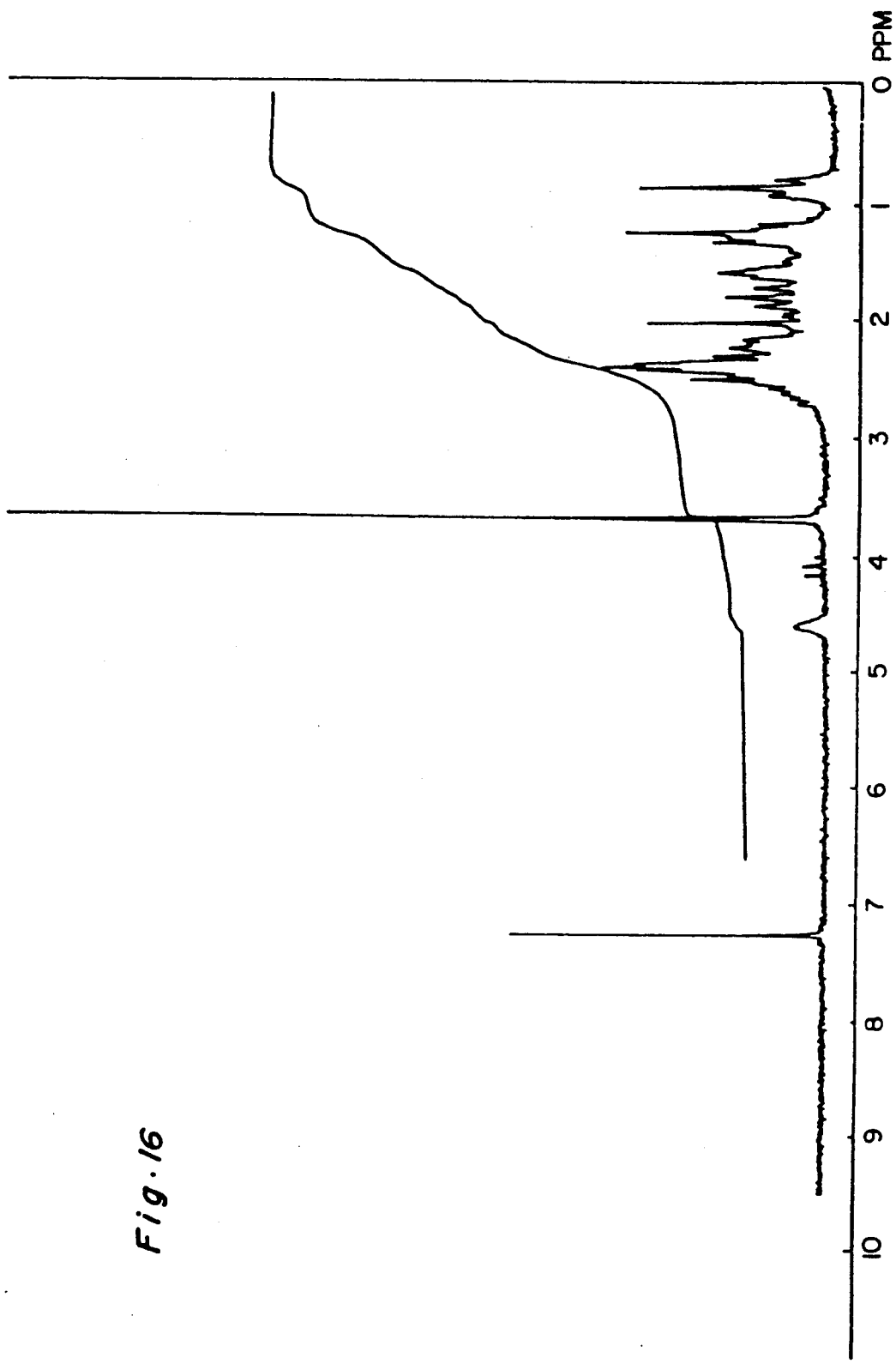

NMR spectrum of (±)-13,14-dihydro-15-keto-5,6-dehydro-PGD$_2$ methyl ester (50) is shown in FIG. 16.

EXAMPLE 17 (CF. SYNTHETIC CHARTS 5 and 6)

Synthesis of 13,14-dihydro-15-keto-5,6-dehydro-PGD$_2$ n-butyl ester (52).

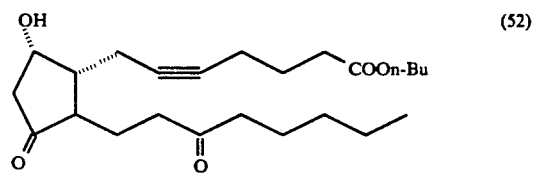

(17-1) Synthesis of 13,14-dihydro-5,6-dehydro-11,15R,S-bis-(t-butyldimethylsilyl)oxy-9-(2-tetrahydropyranyl)oxy-PGF$_{2\alpha}$ (51).

13,14-dihydro-5,6-dehydro-11,15R,S-bis-(t-butyldimethylsilyl)oxy-9-(2-tetrahydropyranyl)oxy-PGF$_{2\alpha}$ methyl ester (47) (0.7580 g) prepared in the same manner as in Example 16 using 4R-t-butyl-dimethylsilyloxy-2-cyclopentenone (43) was converted into carboxylic acid (51) using 20% aqueous solution of sodium hydroxide in methanol. Yield, 0.6202 g.

(17-2) Synthesis of 13,14-dihydro-5,6-dehydro-11,15R,S-bis-(t-butyldimethylsilyl)oxy-9-(2-tetrahydropyranyl)oxy-PGF$_{2\alpha}$ n-butyl ester (52).

Carboxylic acid (51) (0.1660 g) was converted into n-butyl ester (52) using DBU and n-butyl iodide (0.0916 g) in acetonitrile. Yield, 0.1648 g.

The operations of Example 16 were repeated hereafter to give 13,14-dihydro-15-keto-5,6-dehydro-PGD$_2$ n-butyl ester (52).

Figure 15:
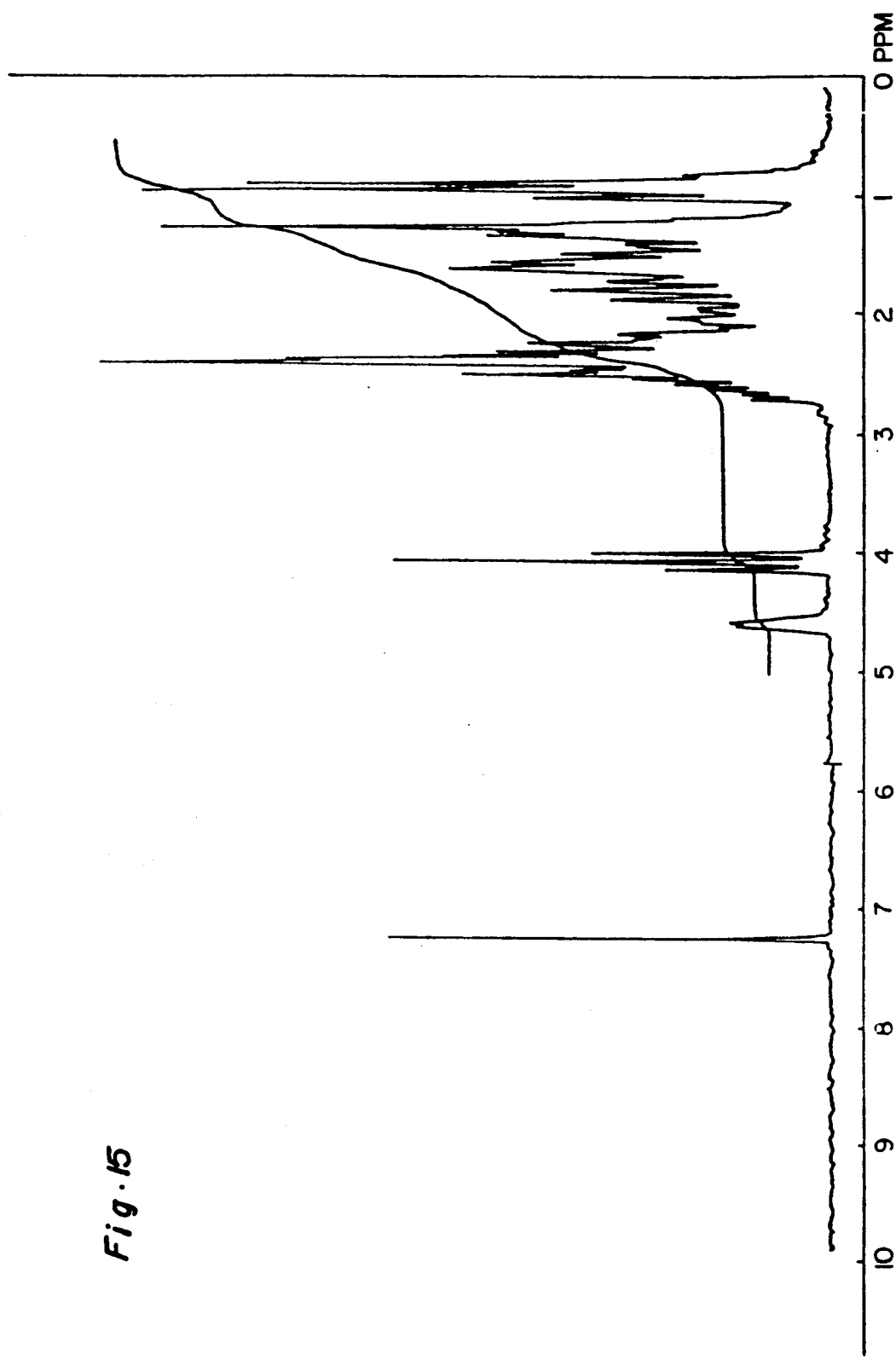

NMR spectrum of 13,14-dihydro-15-keto-5,6-dehydro-PGD$_2$ n-butyl ester (52) is shown in FIG. 15.

EXAMPLE 18 (CF. SYNTHETIC CHARTS 5 and 7)

(18-1) Synthesis of 13,14-dihydro-15-keto-5,6-dehydro-9β-PGD$_2$ methyl ester (59).

13,14-Dihydro-5,6-dehydro-11,15R,S-bis-t-butyl-dimethylsilyloxy-PGE$_2$ (44) obtained in the same manner as in Example 16 using 4R-t-butyl-dimethylsilyloxy- 2-cyclopentenone (43) was reduced with NaBH₄ to give 13,14-dihydro-5,6-dehydro-11,15R,S-bis-t-butyldimethylsilyl-PGF₂β methyl ester (46) (0.2490 g), which was converted into tetrahydropyranyl ether (53) by the conventional method using dihydropyran. Yield, 0.2777 g.

(18-2) Synthesis of 13,14-dihydro-15-keto-5,6-dehydro-11,15R,S-dihydro-9β-(2-tetrahydropyranyl)oxy-PGF₂β methyl ester (54).

The above tetrahydropyranyl ether (53) (0.2777 g) was converted into 13,14-dihydro-15-keto-5,6-dehydro-11,15R,S-dihydro-9β-(2-tetrahydropyranyl)oxy-PGF₂β methyl ester (54) with tetrabutylammonium fluoride (1-M, 6.1 ml) in THF solution (2 ml) at room temperature. Yield, 0.1734 g.

(18-3) Synthesis of 13,14-dihydro-15-keto-5,6-dehydro-9β-(2-tetrahydropyranyl)oxy-PGD₂ methyl ester (58).

The above diol (54) (0.0816 g) was oxidized with Jones reagent (2.67-M, 0.17 ml) in acetone (15 ml) at −30° C. to give 13,14-dihydro-15-keto-5,6-dehydro-9β-(2-tetrahydropyranyl)oxy-PGD₂ methyl ester (58). Yield, 0.0505 g.

(18-4) Synthesis of 13,14-dihydro-15-keto-5,6-dehydro-9β-PGD₂ methyl ester (59).

13,14-Dihydro-15-keto-5,6-dehydro-9β-(2-tetrahydropyranyl)oxy-PGD₂ methyl ester (58) (0.0505 g) was dissolved in a mixed solvent (acetic acid/THF/water (3:3:1)) (6 ml) and allowed to stand at room temperature for 20 hours. After the conventional treatment, the resulting crude product was chromatographed (hexane/ethyl acetate (3:1 -1:1)) to give 13,14-dihydro-15-keto-5,6-dehydro-9β-PGD₂ methyl ester (59). Yield, 0.0314 g.

Figure 17:
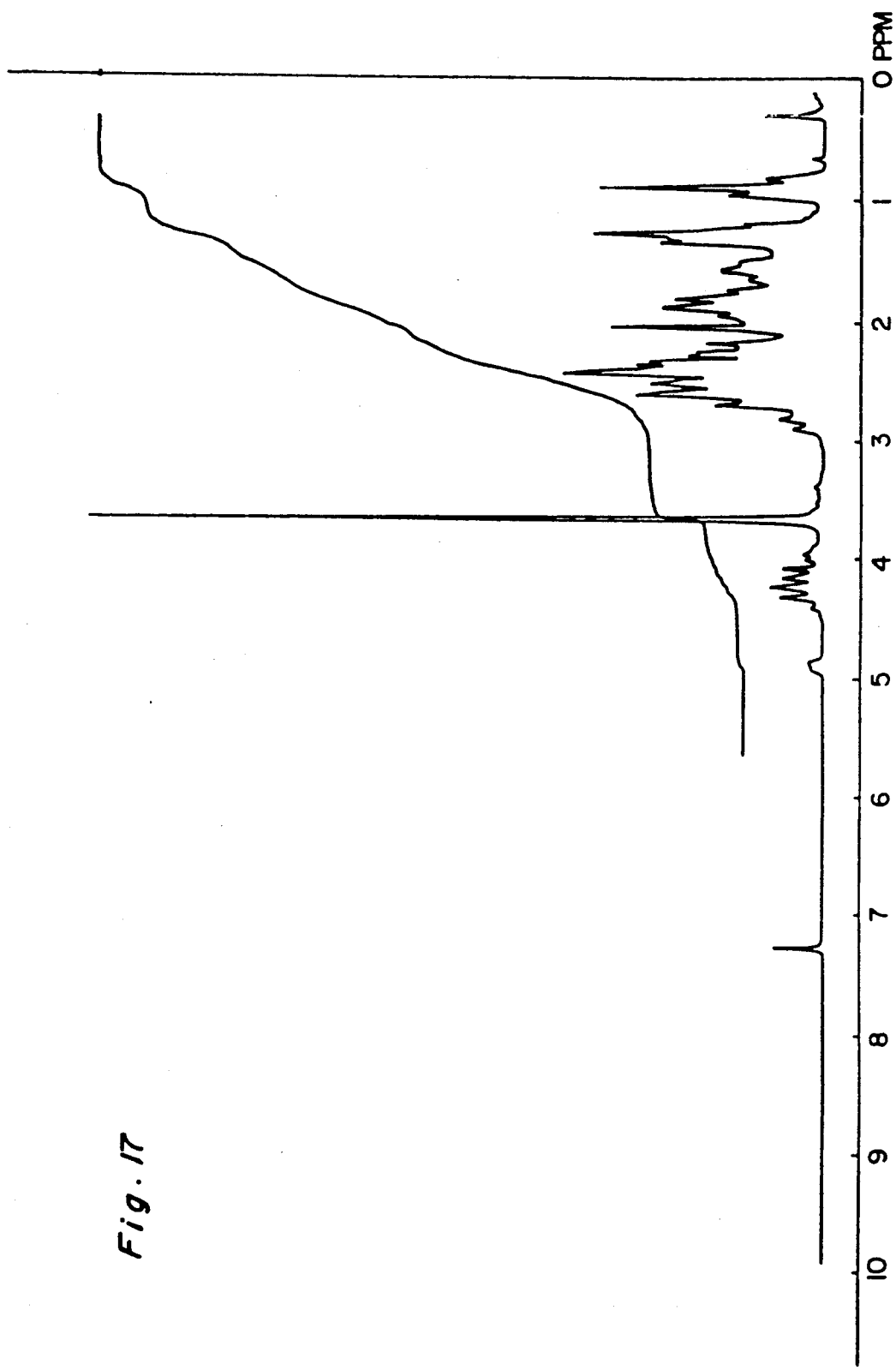

NMR spectrum of 13,14-dihydro-15-keto-5,6-dehydro-9β-PGD₂ methyl ester (59) is shown in FIG. 17.

EXAMPLE 19 (CF. SYNTHETIC CHART 7)

Synthesis of 13,14-dihydro-15-keto-5,6-dehydro-9β-PGD₂ (57).

(19-1) Synthesis of 13,14-dihydro-5,6-dehydro-15R,S-hydroxy-9β-(2-tetrahydropyranyl)oxy-PGF₂β (55).

20% Aqueous sodium hydroxide was added to 13,14-dihydro-5,6-dehydro-15R,S-hydroxy-9β-(2-tetrahydropyranyl)oxy-PGF₂β methylester (54) (0.0893 g) in methanol (4 ml), and the mixture was stirred at room temperature for 2.5 hours. After the conventional treatment, carboxylic acid (55) was obtained. Yield, 0.0787 g.

(19-2) Synthesis of 13,14-dihydro-15-keto-5,6-dehydro-9 β-(2-tetrahydropyranyl)oxy-PGD₂ (56).

The above diol (55) (0.0787 g) was oxidized with Jones reagent (2.67-M, 0.17 ml) in acetone (2 ml) at −40° C. After the conventional treatment, the resulting crude product was chromatographed to give 13,14-dihydro-15-keto-5,6-dehydro-9β-(2-tetrahydropyranyl)oxy-PGD₂ (56). Yield, 0.0344 g.

(19-3) Synthesis of 13,14-dihydro-15-keto-5,6-dehydro-9β-PGD₂ (57).

The above carboxylic acid (56) (0.0344 g) was dissolved in a mixed solvent (acetic acid/THF/water (3:1:1)) (5 ml), and the solution was stirred at room temperature for 21.5 hours. After the conventional treatment, the resulting crude product was chromatographed to give 13,14-dihydro-15-keto-5,6-dehydro-9β-PGD₂ (57). Yield, 0.0152 g.

Figure 18:
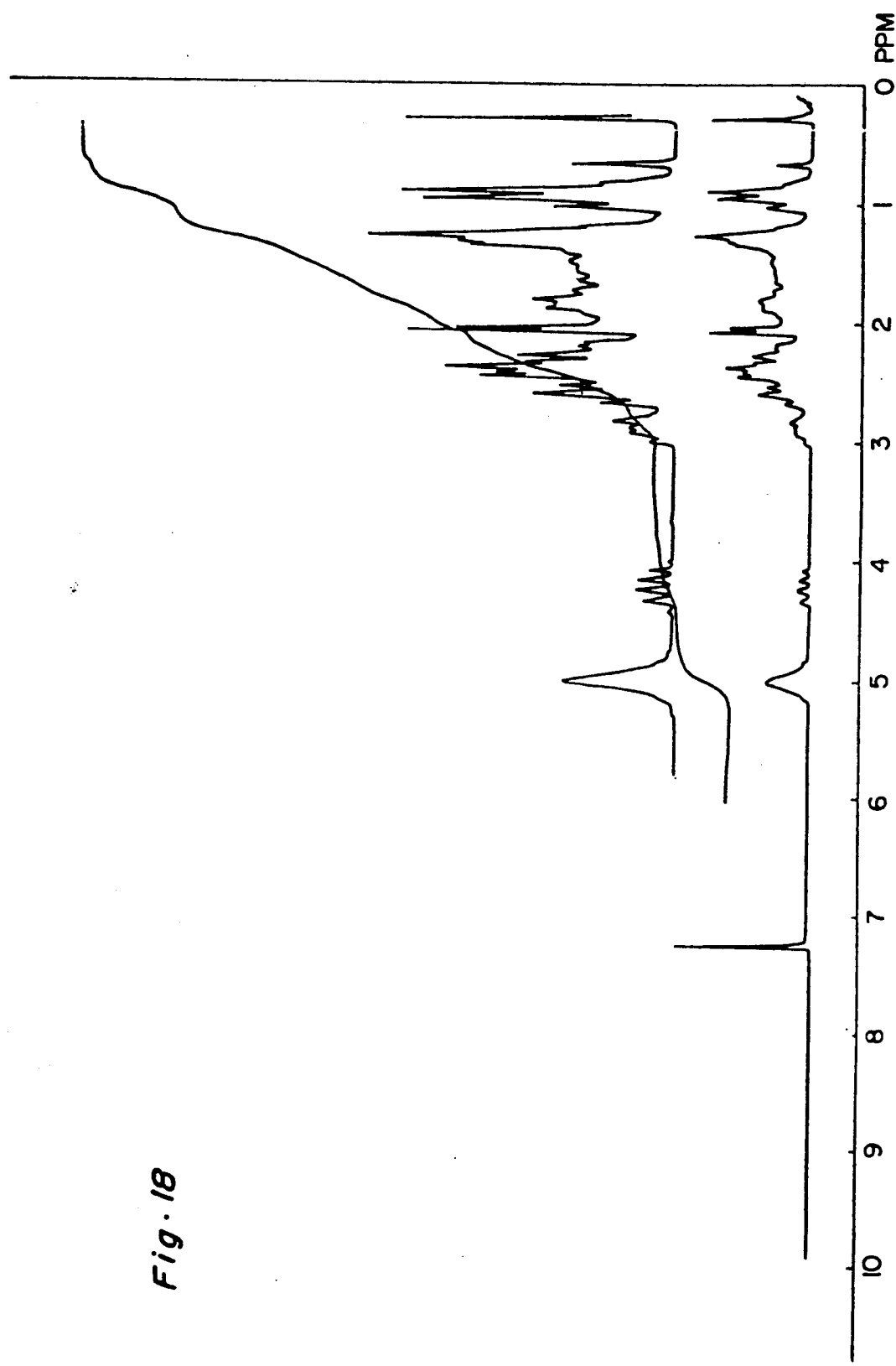

NMR spectrum of 13,14-dihydro-15-keto-5,6-dehydro-9β-PGD₂ (57) is shown in FIG. 18.

EXAMPLE 20

Synthesis of 13,14-dihydro-15-keto-16,16-dimethyl-PGD₂ methyl ester (60).

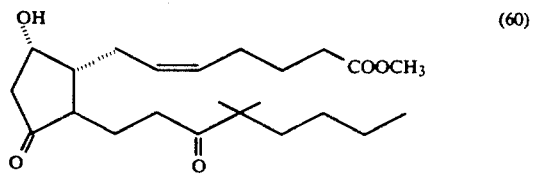

In the same manner as in Example 1 using (−)-Corey lactone (1) and dimethyl(3,3-dimethyl-2-oxoheptyl) phosphonate prepared by the known method, 13,14-dihydro-15-keto-16,16-dimethyl-PGD₂ methyl ester (60) was prepared.

Figure 19:
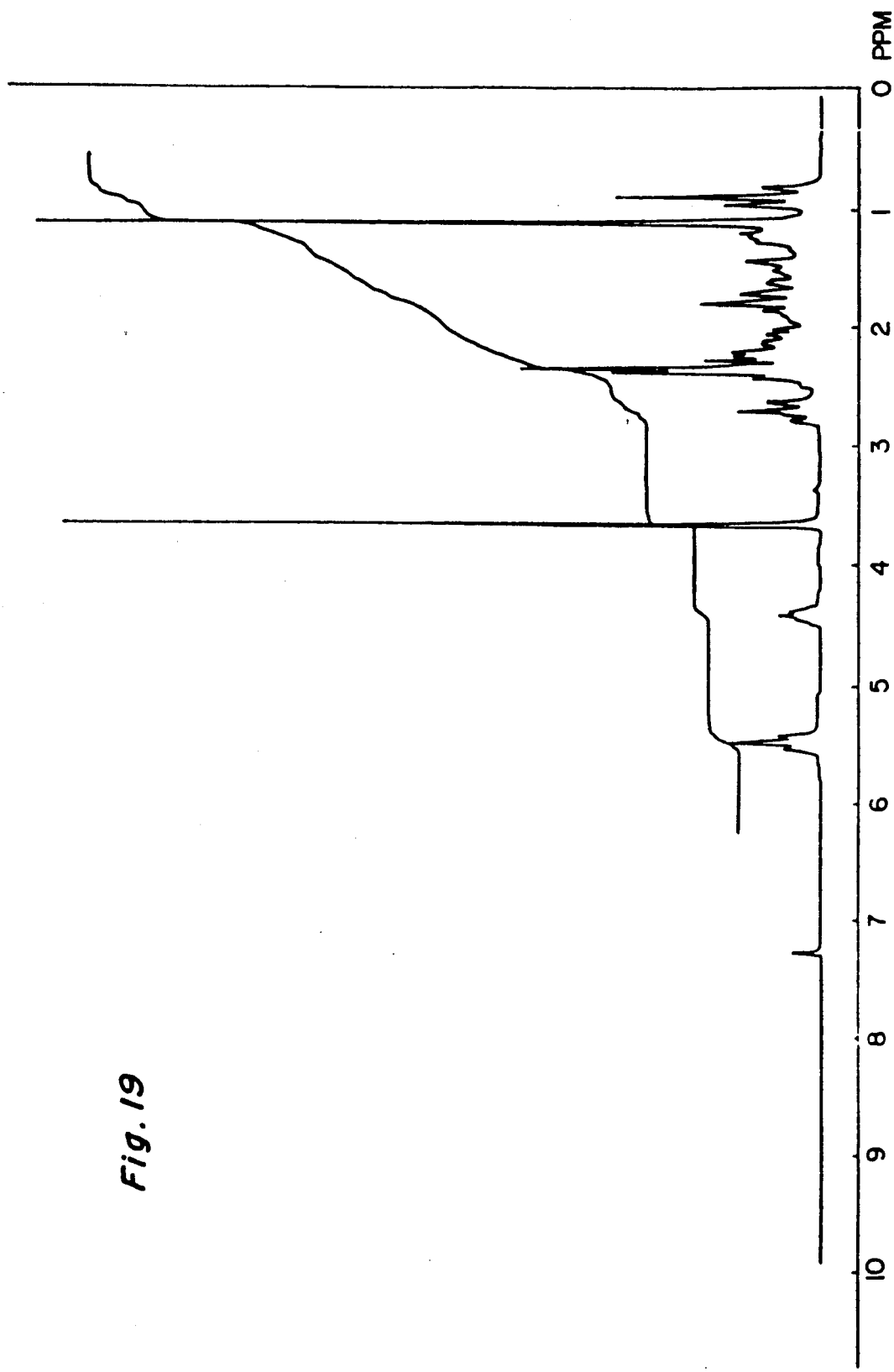

NMR spectrum of 13,14-dihydro-15-keto-16,16-dimethyl-PGD₂ methyl ester (60) is shown in FIG. 19.

EXAMPLE 21 (CF. SYNTHETIC CHART 1)

Synthesis of (±) 13,14-dihydro-15-keto-PGD₂ methyl ester (11), R=Me.

In the same manner as in Example 1 using (±)-Corey lactone, (±) 13,14-dihydro-15-keto-PGD₂ methyl ester (11), R=Me, was prepared.

Figure 20:
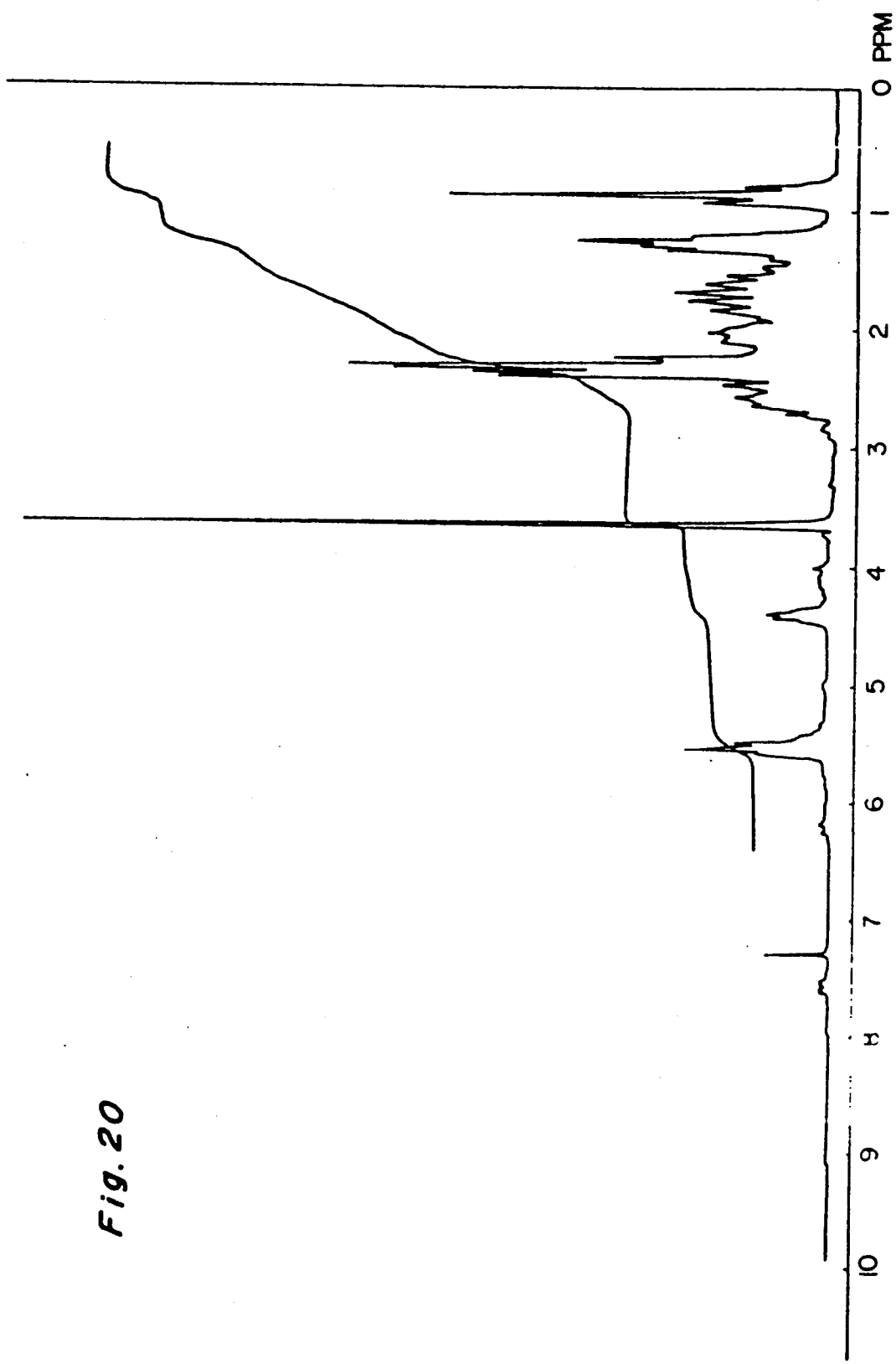

NMR spectrum of 13,14-dihydro-15-keto-PGD₂ methyl ester (11), R=Me, is shown in FIG. 20.

EXAMPLE 22

Synthesis of 13,14-dihydro-15-keto-19-methyl-PGD₂ methyl ester (61).

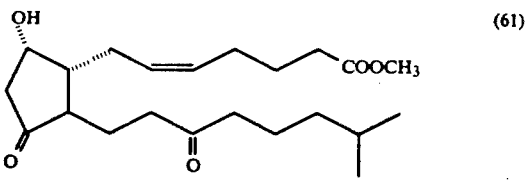

In the same manner as in Example 1 using (−)-Corey lactone (1) and dimethyl(6-methyl-2-oxo-heptyl)phosphonate, 13,14-dihydro-15-keto-19-methyl-PGD₂ methyl ester (61) was prepared.

Figure 21:
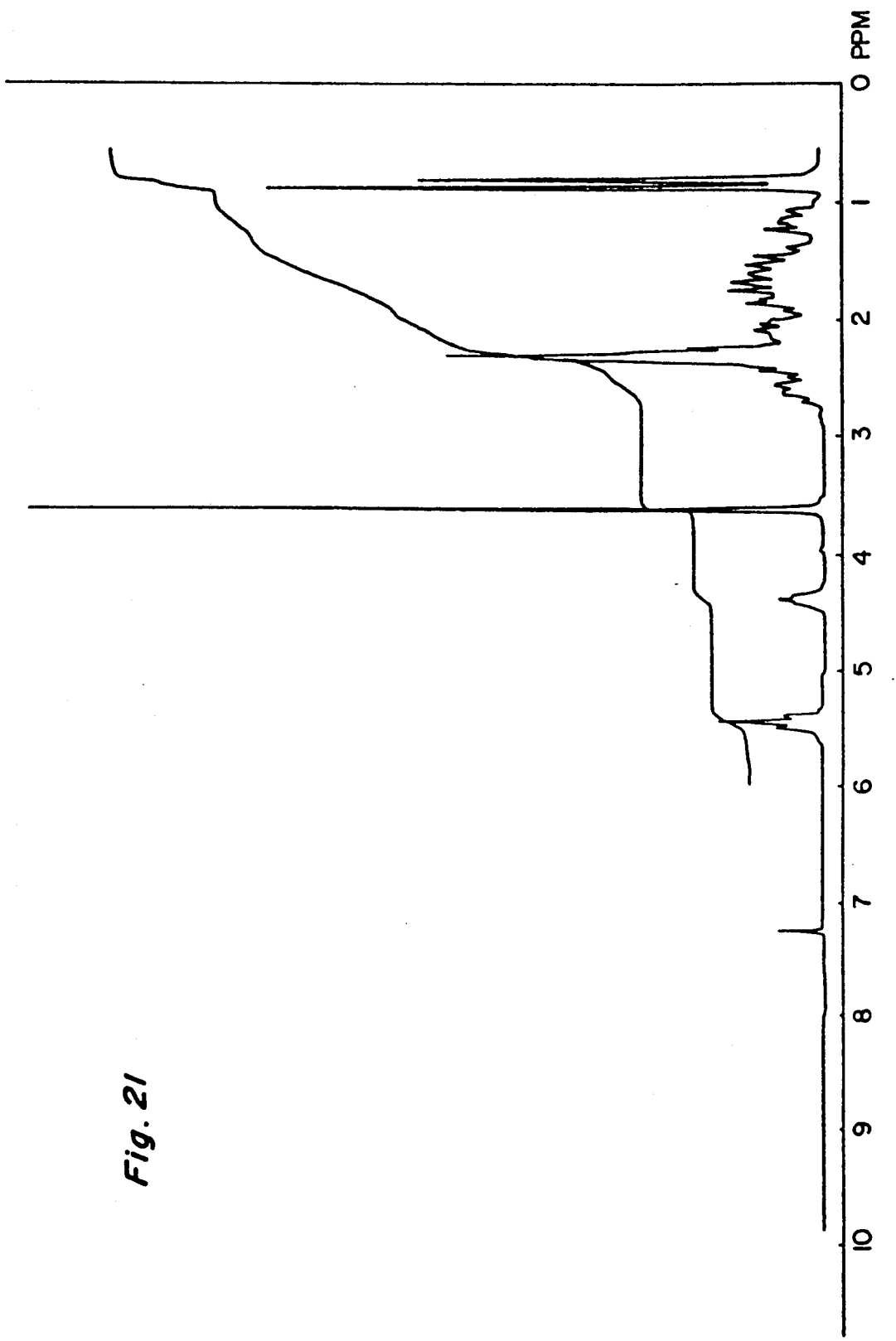

NMR spectrum of 13,14-dihydro-15-keto-19-methyl-PGD₂ methyl ester (61) is shown in FIG. 21.

17

EXAMPLE 23

Synthesis of 13,14-dihydro-15-keto-16,16-dimethyl-20-methoxy-PGD₂ methyl ester (62)

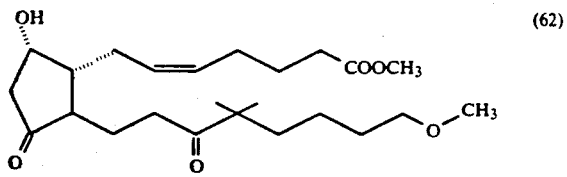

In the same manner as in Examples 1 and 22 using (−)-Corey lactone and dimethyl(3,3-dimethyl-7-methoxy-2-oxoheptyl)phosphonate, 13,14-dihydro-15-keto-16,16-dimethyl-20-methoxy-PGD₂ methyl ester (62) was prepared.

Figure 22:
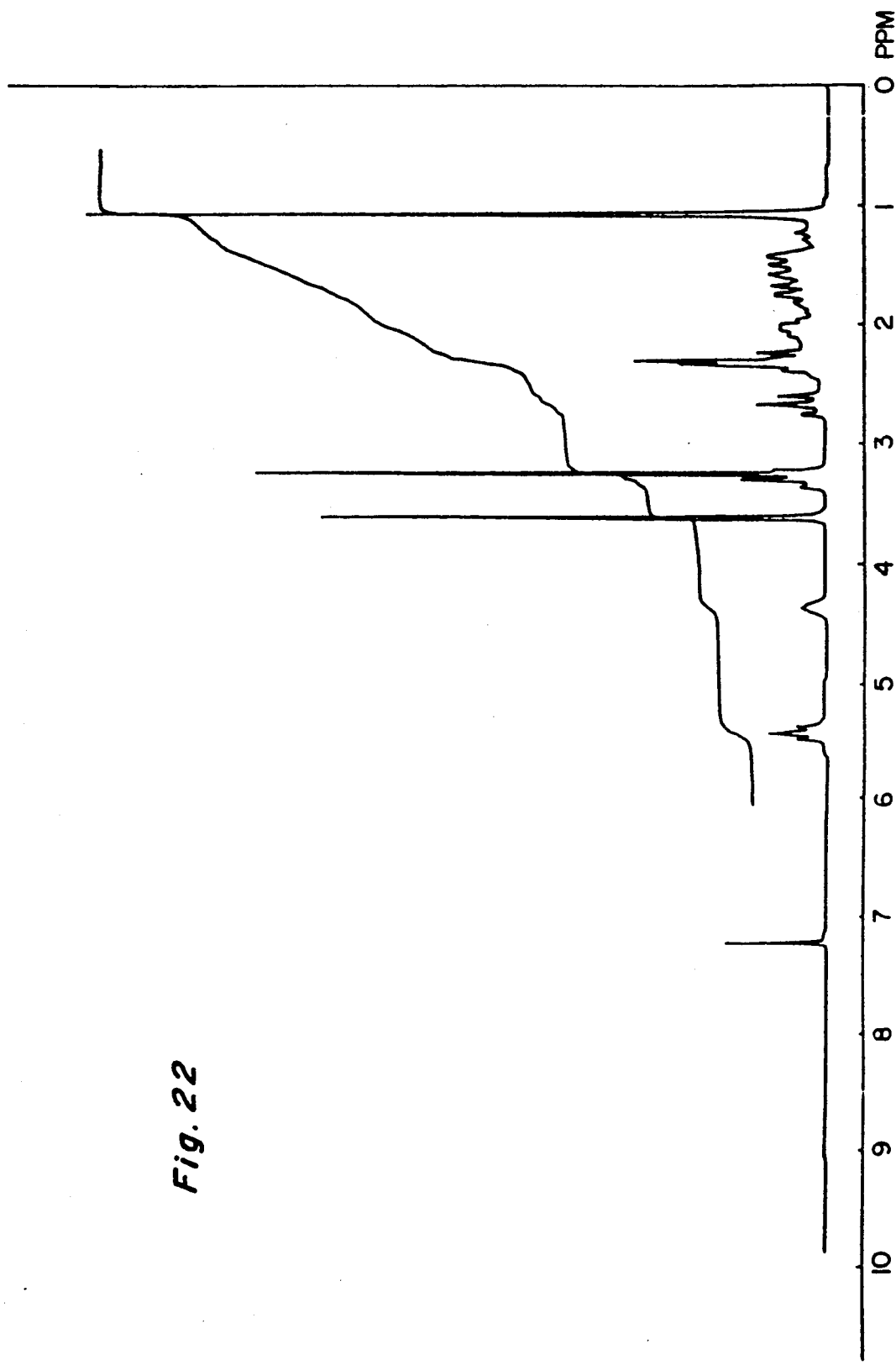

NMR spectrum of 13,14-dihydro-15-keto-16,16-dimethyl-20-methoxy-PGD₂ methyl ester (62) is shown in FIG. 22.

EXAMPLE 24 (CF. SYNTHETIC CHART 8)

Synthesis of 13,14-dihydro-15-keto-16R,S-fluoro-PGD₂ methyl ester (74)

(24-1) Synthesis of 1S-2-oxa-3-oxo-6R-(4R,S-fluoro-3,S-hydroxy-1-octyl)-7R-(p-phenylbenzoyl)oxy-cis-bicyclo(3,3,0)octane (64)

1S-2-oxa-3-oxo-6R-(4R,S-fluoro-3R,S-oxo-1-octyl)-7R-(p-phenylbenzoyl)oxy-cis-bicyclo(3,3,0)octane (63) (2.77 g), which was prepared in the same manner as in Example 1 using (−)-Corey lactone (1) and dimethyl(3R,S-fluoro-2-oxoheptyl)phosphonate, was reduced with NaBH₄ in methanol (90 ml) at 0° C. to give alcohol (64). Yield, 2.91 g.

(24-2) Synthesis of 1S-2-oxa-3-oxo-6R-(4R,S-fluoro-3R,S-hydroxy-1-octyl)-7R-hydroxy-cis-bicyclo-(3,3,0)-octane (65)

The above alcohol (64) (2.91 g) was converted into diol (65) using potassium carbonate (0.82 g) in methanol (120 ml). Yield, 1.61 g.

(24-3) Synthesis of 3R-2-oxa-3-oxo-6R-(4R,S-fluoro-3R,S-t-butyldimethylsilyloxy-1-octyl)-7R-(t-butyldimethylsilyl)oxy-cis-bicyclo(3,3,0)-octane (66)

The above diol (65) (1.61 g) was converted to bis-silylether (66) using t-butyl-dimethylchlorosilane and imidazole in DMF (3 ml). Yield, 2.47 g.

(24-4) Synthesis of 16R,S-fluoro-13,14-dihydro-11,15R,S-bis(t-butyldimethylsilyloxy)-PGF₂α (68)

Bis-silyl ether (66) (2.47 g) was reduced with DIBAL-H according to the conventional method to give lactol (67). Ylide obtained from (4-carboxybutyl)-triphenylphosphonium bromide (6.33 g), sodium hydride (60%, 1.20 g) in DMSO (160 ml), was stirred with lactol (67) in DMSO (60 ml) at room temperature for 15 hours. After the conventional treatment, 0.887 g of 11,15R,S-bis-t-butyldimethylsilyloxy-PGF₂α(68) and 0.996 g of 9,15-bis-t-butyldimethylsilyloxy-PGF₂α(69) were obtained.

18

(24-5) Synthesis of 16R,S-fluoro-13,14-dihydro-11,15R,S-bis-(t-butyldimethylsilyl)oxy-PGF₂αmethyl ester (70)

To 11,15R,S-bis-t-butyldimethylsilyloxy-PGF₂α (68) (0.887 g) were added DBU (0.46 ml) and methane iodide (0.47 ml) in acetonitrile (25 ml), and the mixture was held at 40° C. for 3.5 hours. According to the conventional treatment, methyl ester (70) was obtained. Yield, 0.738 g.

(24-6) Synthesis of tetrahydropyranyl ether (71)

The above methyl ester (70) was converted into tetrahydropyranyl ether (71) using dihydropyran and p-toluenesulfonic acid.

(24-7) Synthesis of 16R,S-fluoro-13,14-dihydro-15R,S-hydroxy-9-(2-tetrahydropyranyl)oxy-PGF₂α methyl ester (72)

The above pyranyl ether (71) was dissolved in THF (20 ml), to which was added a solution of tetrabutylammonium fluoride in THF (1.0-M, 18 ml). The resulting solution was stirred at room temperature for 2 hours. The crude product obtained by the conventional treatment was chromatographed (hexane/ethyl acetate (2:1–1:1)) to give 16R,S-fluoro-13,14-dihydro-15R,S-hydroxy-9-(2-tetrahydropyranyl)oxy-PGF₂α methyl ester (72). Yield, 0.487 g.

(24-8) Synthesis of 13,14-dihydro-15-keto-16R,S-fluoro-9-(2-tetrahydropyranyl)oxy-PGD₂ methyl ester (73)

The above diol (72) (0.487 g) was oxidized with Jones reagent (2.67-M, 1.19 ml) in acetone (45 ml) at −20° C. After the conventional treatment, the resulting crude product was chromatographed (hexane/ethyl acetate (5:1)) to give 13,14-dihydro-15-keto-16R,S-fluoro-9-(2-tetrahydropyranyl)oxy-PGD₂ methyl ester (73). Yield, 0.373 g.

(24-9) Synthesis of 13,14-dihydro-15-keto-16R,S-fluoro-PGD₂ methyl ester (74)

The above tetrahydropyranyl ether (73) (0.373 g) was dissolved in a mixed solvent (acetic acid/THF/water (3:1:1)) (25 ml) and held at 45° C. for 7 hours. After the conventional treatment, the resulting crude product was chromatographed (hexane/ethyl acetate (4:1)) to give 13,14-dihydro-15-keto-16R,S-fluoro-PGD₂ methyl ester (74). Yield, 0.221 g.

The NMR data of 13,14-dihydro-15-keto-16R,S-fluoro-PGD₂-methyl ester (74) is as follow: $\sigma$:0.91(3H, t, J=6 Hz), 1,1–2.93(23H, m), 2.64(3H, s), 4.3–4.5(1.5H, m), 4.98(0.5H, dd, J=6 Hz), 5.50(2H, m).

EXPERIMENT 1

Sleep-Inducing Action by the Administration of 13,14-dihydro-15-keto-PGDs into Cerebral Third Ventricle As test samples PGD₂ was purchased from Funakoshi Yakuhin K. K. and 13,14-dihydro-15-keto-PGD₂ was obtained from the above Examples.

Male rats of SD strain (weight: 350–400 g) were used as test animals.

The electroencephalogram was bipolarly recorded with screw electrodes fixed to the frontal part of the skull chronically. The electrodes for recording electromyogram were inserted into musculus tibialis posterior and fixed.

A cannula (diameter: 0.35 mm) of stainless steel was inserted into the cerebral third ventricle for administration of the test samples.

The experiments were made after elapse of at least one week of convalescence of rats after operation under the condition that the rats could freely move in cages of 25 cm (D)×25 cm (W)×45 cm (H).

Each test sample was dissolved in sterilized phisiological saline. The obtained each solution was injected into the cerebral third ventricle of the test animals separately at a rate of 20 μl/hour during 10 hours from 20:00–6:00 o'clock. As a control group, rats were administered physiological saline one day before the administration of the test samples.

The amount of sleep of rats was determined from the electroencephalogram and electromyogram recorded on the polygraph over 24 hours. Slow wave sleeping amount was determined using the slow wave with high amplitude as an indicator.

Figure 23:
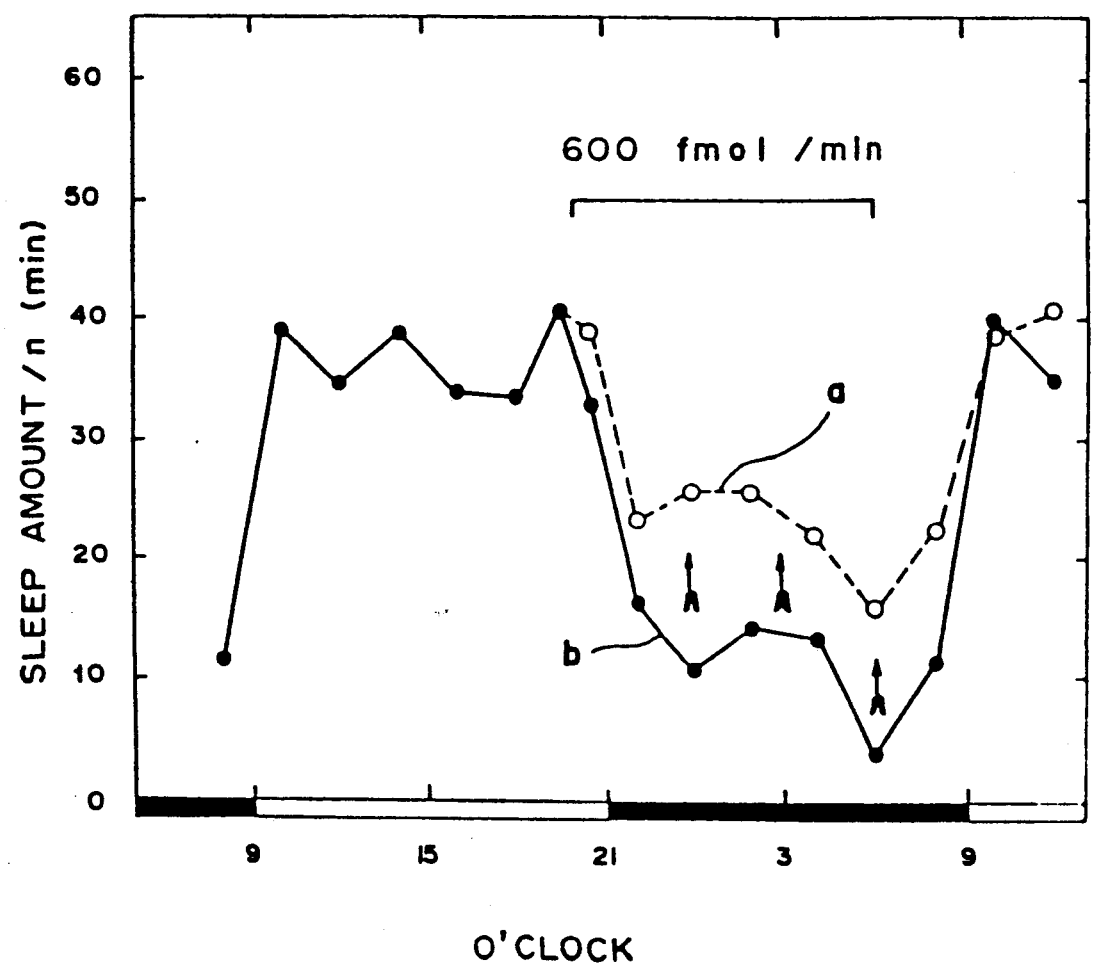
FIG. 23 shows a sleep inducing action of 13,14-dihydro-15-keto-PGD$_2$.

The result from the administration of 13,14-dihydro-15-keto-$PGD_2$ is shown in FIG. 23, in which (a) shows the results from 13,14-dihydro-15-keto-$PGD_2$ and (b) shows the results from the administration of the physiological saline.

FIG. 23 indicates that the amount of the sleep increased by the administration of 13,14-dihydro-15-keto-$PGD_2$ into cerebral ventricles.

The results are also shown in Table 1.

EXPERIMENT 2

Sleep-Inducing Action Caused through Peripheral Administration (Oral, Intravenous and Subcutaneous Administration) of 13, 14-dihydro-15-keto-PGDs As test samples 13,14-dihydro-15-keto-PGDs obtained in above Examples and $PGD_2$ (available from Funakoshi Yakuhin K. K.) as control reference were used. Five weeks aged, male mice of the Slc-ddy strain were employed as test animals. The electroencephalogram was bipolarly recorded with electrodes fixed to the frontal part of the skull. Electromyogram was recorded with electrodes fixed in the musculus tibialis posterior.

Mi. were used after elapse of at least one week of convalencence. Each test animal was placed on a triangular platform (10 cm×10 cm×10 cm) being set 30 cm high from the floor, with their levels of wakefulness being maintained in the excited state.

Oral administration was conducted by dissolving test sample in physiological saline containing 0.5% of carboxymethylcellulose in the ratio of 10 ml/kg. Intravenous administration was carried out by giving a solution of a test sample in physiological saline through a tail vein. Each group of test animals employed consisted of three to five mice.

A test sample was administered to mice 20 minutes after having been placed on the platform, and the polygraphic recordings of electroencephalograms and electromyograms were carried out over the 80 minutes period thereafter.

On the bases of the recordings obtained, the levels of wakefulness and/or sleep are classified into the following four categories. Thus, (i) the aroused wave stage (AW) where the electroencephalogram exhibits low amplitude and high frequency waves mostly ranging from 7 to 8 HZ, while the clear-appearance of electromyogram is revealed; (ii) the slow wave light sleep stage (SWLS) where the electroencephalogram is observed to produce a change toward higher-amplitude slower waves (not greater than 4 HZ), but for the duration of not longer than 30 seconds; (iii) the slow wave deep sleep stage (SWDS) where the electroencephalogram causes a change toward higher-amplitude slower waves with its duration being greater than 30 seconds; and (iv) the paradoxical sleep stage (PS) where the electroencephalogram constitutes low-amplitude fast wave, with the entirely disappeared electromyographic signal. In FIGS. 24 to 27, the arrow mark denotes a point of time when test sample was given.

Figure 24:
FIG. 24–FIG. 27 show results of sleep-elapse change after administration of 13,14-dihydro-15-keto-PGDs.
Figure 25:
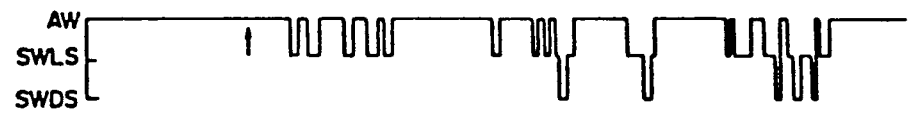

FIG. 24 shows the result of sleep-elapse change when the physiological saline was intravenously administered, and FIG. 25 shows the result when the methyl ester of 13,14-dihydro-15-keto-$PGD_2$ (5 mg/kg) was intravenously administered. As apparent from FIG. 24 the administration of physiological saline did not cause SWDS, whereas the methyl ester of 13,14-dihydro-15-keto-$PGD_2$ (5 mg/kg administration) induced sleep with SWDS. Similar thereto 5 mg/kg administration of ethyl ester of 13,14-dihydro-15-keto-$PGD_2$ and n-butyl ester of 13,14-dihydro-15-keto-$PGD_2$ induced sleep with SWDS respectively.

Figure 26:
Figure 27:

FIG. 26 shows the result of sleep-elapse change when a physiological saline containing 0.5% of carboxymethylcellulose was orally administered, and FIG. 27 shows the result when 5 mg/kg of methyl ester of 13,14-dihydro-15-keto-20-methoxy-$PGD_2$ was orally administered. As apparent from the both figures the former did not induce SWDS whereas the latter induce sleep with SWDS. Similar to the above the oral administration of methyl ester of 13,14-dihydro-15-keto-3R,S-methyl-20-methoxy-$PGD_2$ and methyl ester of 13,14-dihydro-18-methoxy-18,19-dinor-$PGD_2$ (5 mg/kg) induced sleep with SWDS.

The oral administration of ethyl ester of 13,14-dihydro-15-keto-20-methoxy-$PGD_2$ induced sleep with SWDS in 10 mg/kg. Other test samples, 13,14-dihydro-15-keto-PGDs, showed sleep inducing action with SWDS through oral administration of 10 mg/kg.

The results of the above experiment as to the sleep inducing action are shown in Table 1, wherein "+" exhibits the presence of sleep inducing action with SWDS and "−" exhibits the absence of sleep inducing action with SWDS.

EXPERIMENT 3

Sedation by 13,14-dihydro-15-keto-PGDs through Administration of Cisterna Magma

As test samples there were used 13,14-dihydro-15-keto-$PGD_2$, methyl ester of 13,14-dihydro-15-keto-$PGD_2$, ethyl ester of 13,14-dihydro-15-keto-$PGD_2$, and n-butyl ester of 13,14-dihydro-15-keto-$PGD_2$ as embodiments of the present invention, and $PGD_2$ (available from Funakoshi Yakuhin K. K.) and physiological saline as comparative experiments.

Each test sample (1 mg) was dissolved in ethyl alcohol (1 ml) to prepare each solution, a given amount of which was taken into test tubes respectively. The solution was dried under nitrogen stream, to which sterile physiological saline was added and then subjected to ultrasonic wave to form micells. Ten μl of each solution of the test sample was administered into cisterna magma, and as a comparative experiment 10 μl of physiological saline was administered.

As test animals 4 to 6 male mice of ddY strain (weight: 32-34 g) were employed.

The amount of movement of test mice was determined by Automex II (available from Colombus Instruments Co.). The amount was expressed by "counts". The less counts indicates the higher action of sedative activity.

13,14-dihydro-15-keto-PGD$_2$, methyl ester 13,14-dihydro-15-keto-PGD$_2$, ethyl ester of 13,14-dihydro-15-keto-PGD$_2$, and n-butyl ester of 13,14-dihydro-15-keto-PGD$_2$ exhibited sedation at 0.2 mg/kg and PGD$_2$ did at 0.02 mg/kg. The results are shown in Table 1.

EXPERIMENT 4

Sedative Activity Caused through Peripheral Administration (Oral, Intravenous and Subcutaneous Administration) of 13,14-dihydro-15-keto-PGDs As test and control reference samples, there were used the same compounds as in Experiment 2.

Each group of test animals used consisted of 6 to 14 five-week aged, male mice of the Slc-ddY strain.

In order to measure the amounts of activities of mice, MK-Animex (Animex Activity Meter, Model KSE: available from Muromachi Kikai K. K.) was employed to take measurements of the amounts of activities as a count, whereby the decrease in the amounts of activities indicated the presence of sedative activity.

The above-described test samples were given to mice and evaluated for the development of sedative activity, with the evaluation results shown in Table 1.

PGD$_2$ exhibited sedative activity by the intravenous administration of 1 mg/kg, but 13,14-dihydro-15-keto-PGD$_2$ did not exhibited the same activity even by the administration of 5 mg/kg. Methyl ester, ethyl ester and n-butyl ester of 13,14-dihydro-15-keto-PGD$_2$ exhibited the sedative activity by the intravenous administration of 5 mg/kg respectively.

Methyl ester of 13,14-dihydro-15-keto-20-methoxy-PGD$_2$ exhibited sedative activity by oral administration of 5 mg/kg as well as intravenous administration of 1 mg/kg. Methyl ester of 13,14-dihydro-15-keto-3R,S-methyl-20-methoxy-PGD$_2$ exhibited sedative activity by the oral administration of 5 mg/kg. The other test sample exhibited sedative activity by the intravenous administration of 10 mg/kg.

TABLE 1

| Sample | Induction of Sleep | | Sedative Effect (Inhibition of Ultromotivity) | |
|---|---|---|---|---|
| 1 | i.C.V. | [1]600 fmol/min + | i.Cist | [2]0.2 mg/kg + |
|  |  |  | I.V. | 5 mg/kg − |
| 2 |  |  | i.Cist | 0.2 mg/kg + |
|  | I.V. | 5 mg/kg + | I.V. | 5 mg/kg + |
| 3 |  |  | i.Cist | 0.2 mg/kg + |
|  | I.V. | 5 mg/kg + | I.V. | 5 mg/kg + |
| 4 |  |  | i.Cist | 0.2 mg/kg + |
|  | I.V. | 5 mg/kg + | I.V. | 5 mg/kg + |
| 5 | P.O.[3] | 5 mg/kg + | P.O. | 5 mg/kg + |
|  |  | 3 mg/kg ± |  |  |
|  |  | 1 mg/kg − | I.V. | 1 mg/kg + |
|  | I.V.[4] | 5 mg/kg + |  | 5 mg/kg + |
| 6 | P.O. | 5 mg/kg + | P.O. | 5 mg/kg + |
|  |  | 3 mg/kg − |  |  |
| 7 | P.O. | 10 mg/kg + | I.V. | 10 mg/kg + |
|  |  | 5 mg/kg + |  |  |
|  |  | 3 mg/kg − |  |  |
| 8 | P.O. | 10 mg/kg + | I.V. | 10 mg/kg + |
|  |  | 5 mg/kg ± |  |  |
|  |  | 3 mg/kg − |  |  |
| 9 | P.O. | 10 mg/kg + | I.V. | 10 mg/kg + |
| 10 | P.O. | 10 mg/kg + | I.V. | 10 mg/kg + |

TABLE 1-continued

| Sample | Induction of Sleep | | Sedative Effect (Inhibition of Ultromotivity) | |
|---|---|---|---|---|
| 11 | P.O. | 10 mg/kg + | I.V. | 10 mg/kg + |
| 12 | P.O. | 10 mg/kg + | I.V. | 10 mg/kg + |
| 13 | P.O. | 10 mg/kg + | I.V. | 10 mg/kg + |
| 14 | P.O. | 10 mg/kg + | I.V. | 10 mg/kg + |
| 15 | P.O. | 10 mg/kg + | I.V. | 10 mg/kg + |
| 16 | P.O. | 10 mg/kg + | I.V. | 10 mg/kg + |
| 17 | P.O. | 10 mg/kg + | I.V. | 10 mg/kg + |
| 18 | P.O. | 10 mg/kg + | I.V. | 10 mg/kg + |
| 19 | P.O. | 10 mg/kg + | I.V. | 10 mg/kg + |
| Ref. Ex. |  |  |  |  |
| 20 | i.C.V. | 600 fmol/min + | i.Cist | 0.02 mg/kg + |
|  | P.O. | 5 mg/kg − | P.O. | 10 mg/kg − |
|  | I.V. | 1 mg/kg − | I.V. | 1 mg/kg + |
|  | S.C.[5] | 0.5 mg/kg − | S.C. | 0.5 mg/kg + |
| 21 | P.O. | 10 ml/kg − | P.O. | 20 ml/kg − |
|  | I.V. | 10 ml/kg − | I.V. | 10 ml/kg − |
|  |  |  | S.C. | 10 mg/kg − |

Samples:
1: 13,14-dihydro-15-keto-PGD$_2$
2: 13,14-dihydro-15-keto-PGD$_2$ methyl ester
3: 13,14-dihydro-15-keto-PGD$_2$ ethyl ester
4: 13,14-dihydro-15-keto-PGD$_2$ n-butyl ester
5: 13,14-dihydro-15-keto-20-methoxy-PGD$_2$ methyl ester
6: 13,14-dihydro-15-keto-3R,S-methyl-20-methoxy-PGD$_2$ methyl ester
7: 13,14-dihydro-15-keto-18-methoxy-19,20-bisnor-PGD$_2$ methyl ester
8: 13,14-dihydro-15-keto-20-methoxy-PGD$_2$ ethyl ester
9: 13,14-dihydro-15-keto-20-methoxy-PGD$_2$ n-butyl ester
10: 13,14-dihydro-15-keto-20-methoxy-PGD$_2$
11: 13,14-dihydro-15-keto-20-methoxy-$\Delta^2$-PGD$_2$ methyl ester
12: 13,14-dihydro-15-keto-16R,S-methyl-20-methoxy-PGD$_2$ methyl ester
13: 13,14-dihydro-15-keto-20-methoxyethyl-PGD$_2$ methyl ester
14: 13,14-dihydro-15-keto-19-ethoxy-20-nor-PGD$_2$ methyl ester
15: 13,14-dihydro-15-keto-19-ethoxy-20-nor-PGD$_2$ n-butyl ester
16: 13,14-dihydro-15-keto-16,16-dimethyl-20-methoxy-PGD$_2$ methyl ester
17: 13,14-dihydro-15-keto-19-methyl-PGD$_2$ methyl ester
18: 13,14-dihydro-15-keto-16R,S-fluoro-PGD$_2$ methyl ester
19: 13,14-dihydro-15-keto-5,6-dehydro-9R-PGD$_2$ methyl ester
Ref. Ex. 20: PGD$_2$ (manufactured by Funakoshi Yakuhin K.K.)
21: Physiological saline
[1]intraventricular administration
[2]intrapostcisternal administration
[3]oral administration
[4]intravenous injection
[5]subcutaneous injection

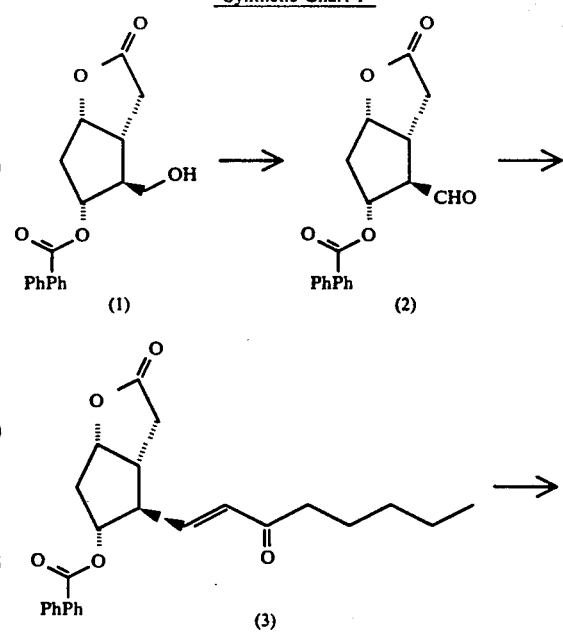

Synthetic Chart 1

-continued
Synthetic Chart 1
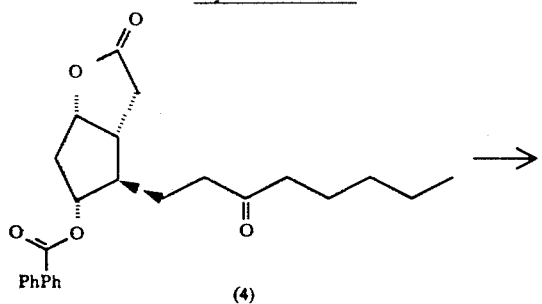
(4)
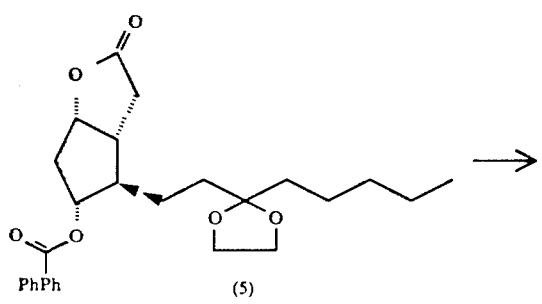
(5)
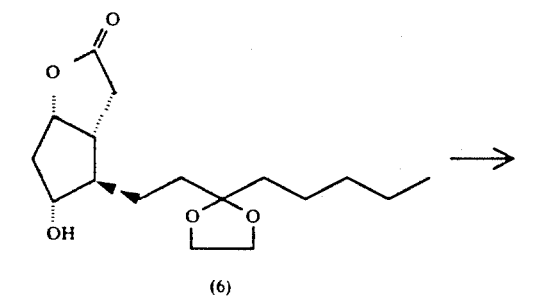
(6)
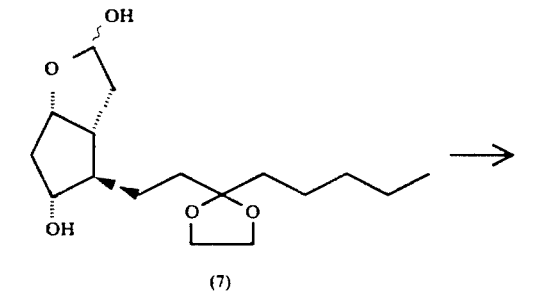
(7)
-continued
Synthetic Chart 1
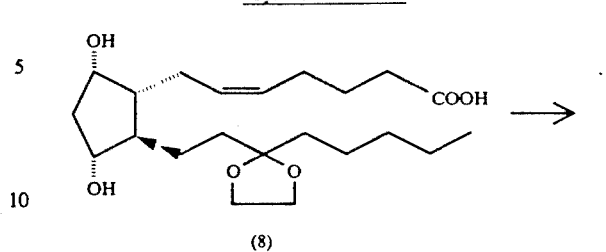
(8)
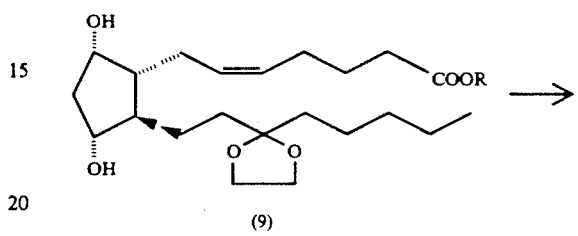
(9)
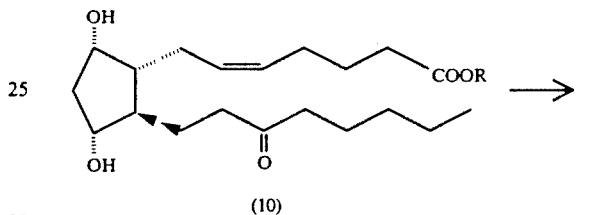
(10)
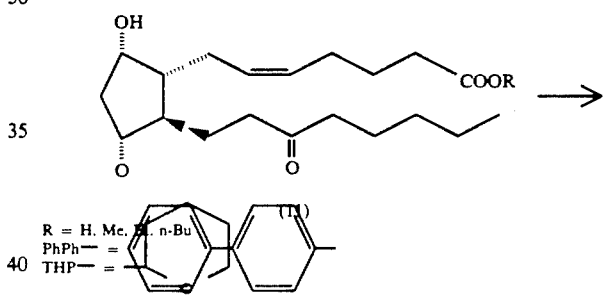
(11)
R = H, Me, n-Bu
PhPh— =
THP— =
Synthetic Chart 2
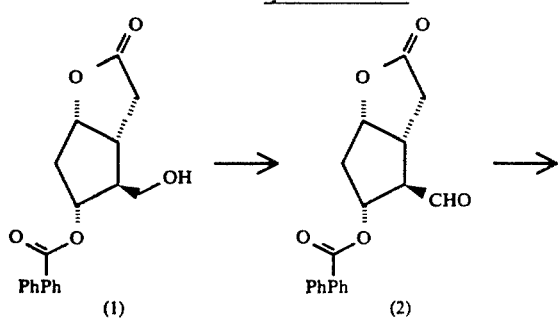
(1)  (2)

Synthetic Chart 2
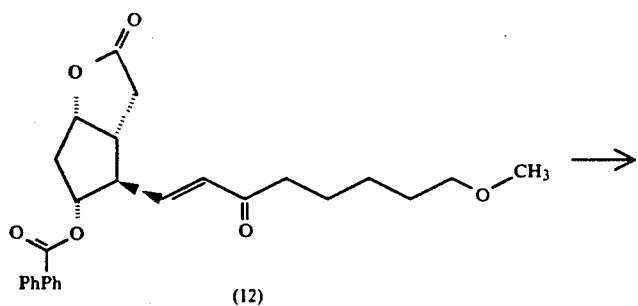
(12)
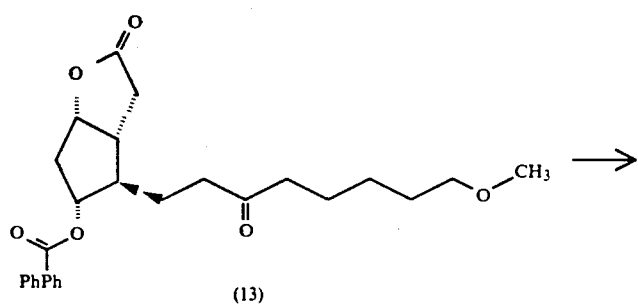
(13)
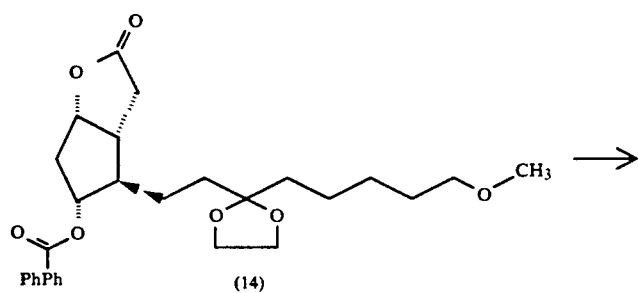
(14)
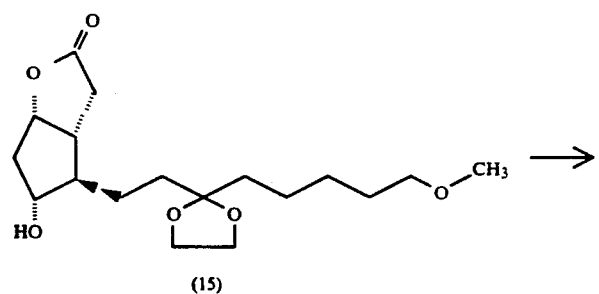
(15)
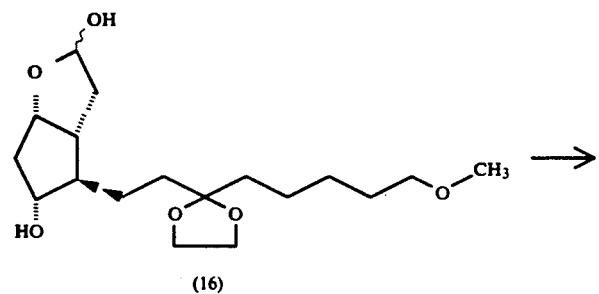
(16)

Synthetic Chart 2
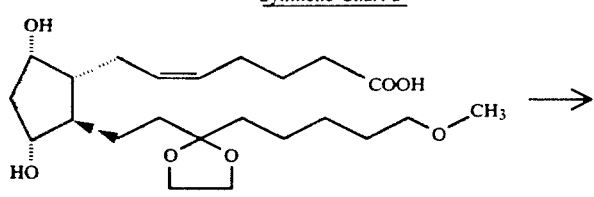
(17)
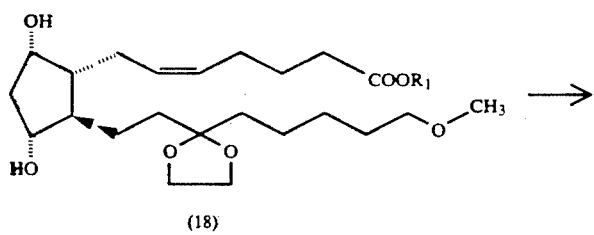
(18)
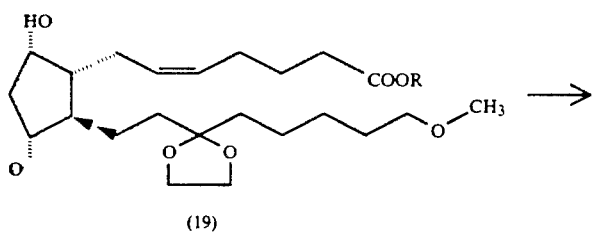
(19)
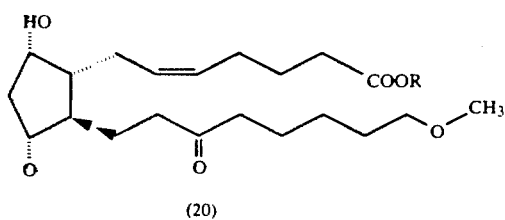
(20)
R: Me, Et, n-Bu
Synthetic Chart 3
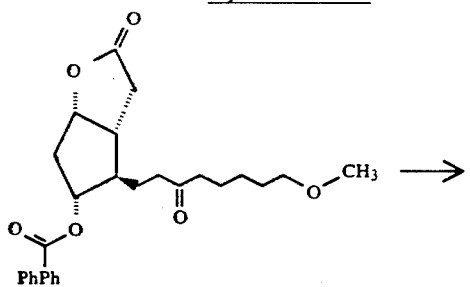
(13)
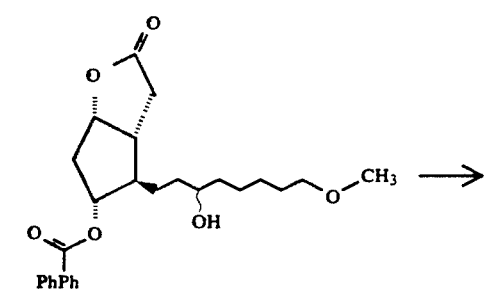
(21)
-continued
Synthetic Chart 3
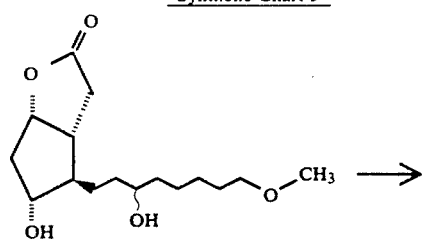
(22)
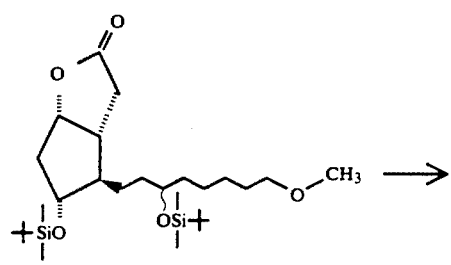
(23)

Synthetic Chart 3 -continued
Synthetic Chart 4
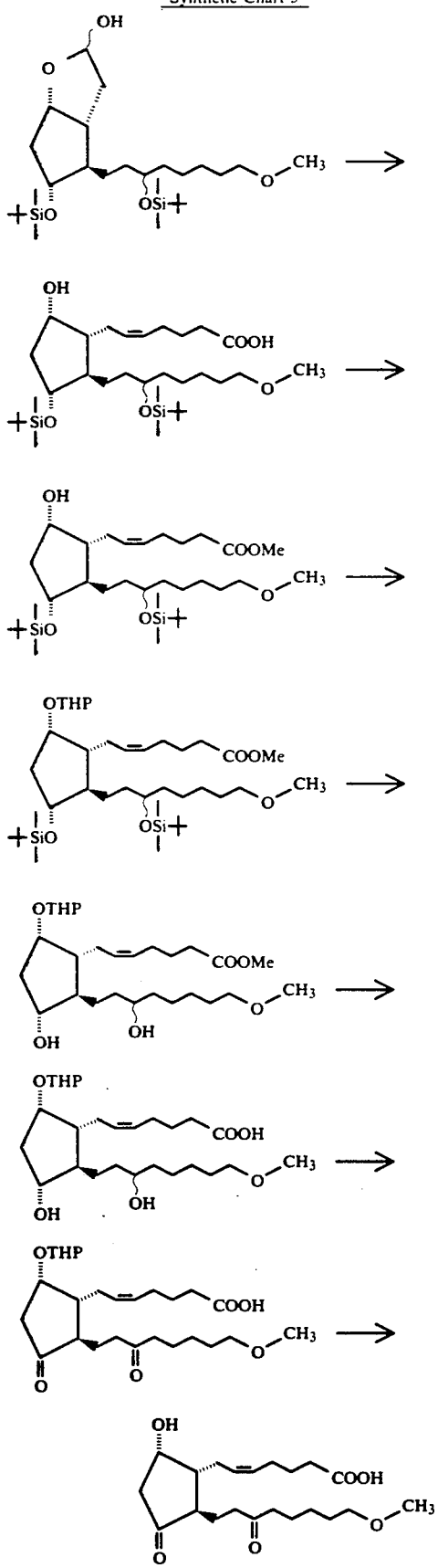
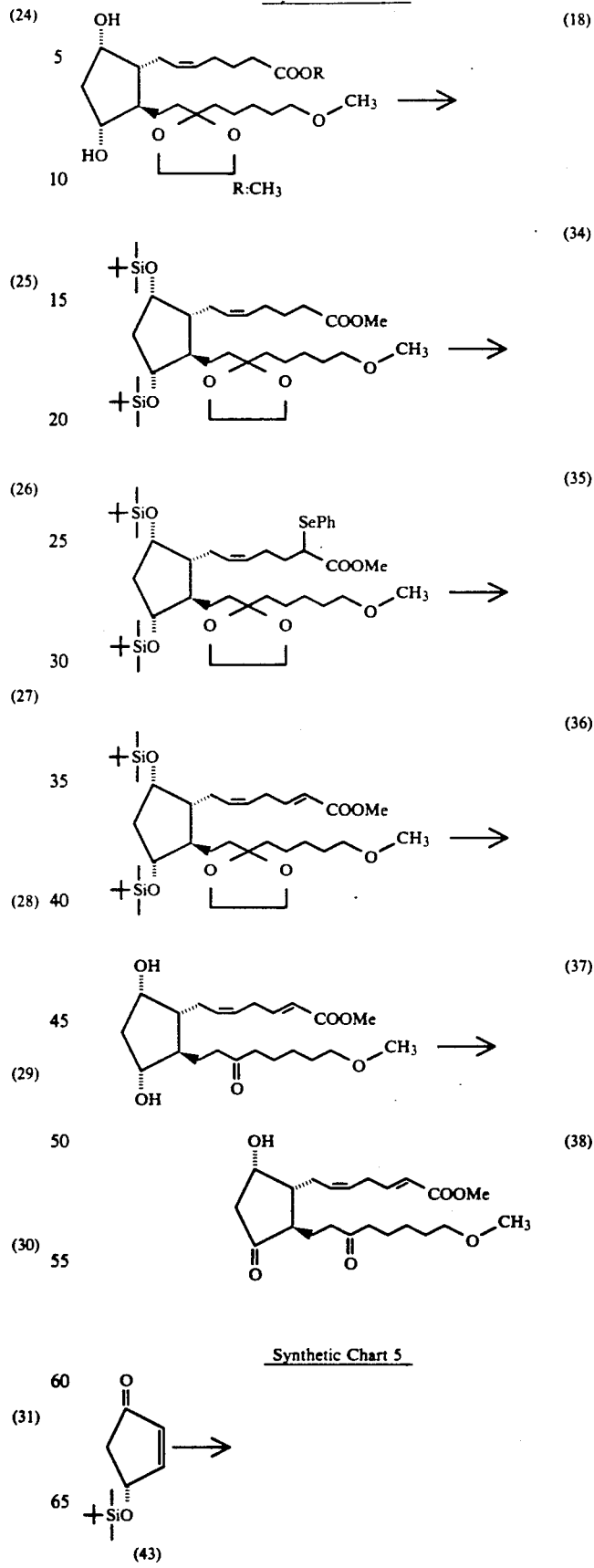
Synthetic Chart 5

-continued
Synthetic Chart 5
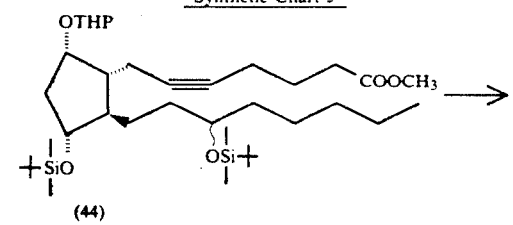
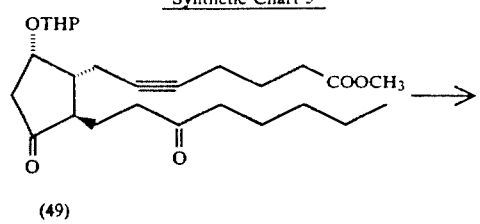
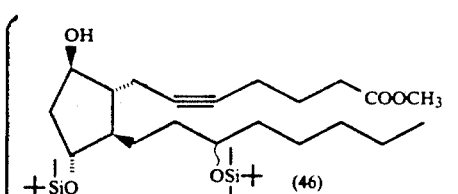
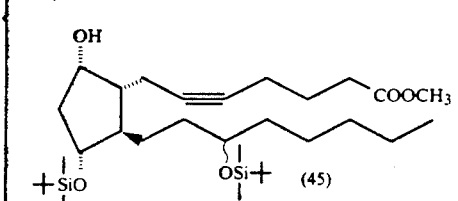
Synthetic Chart 6
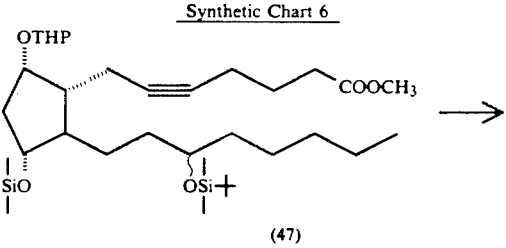
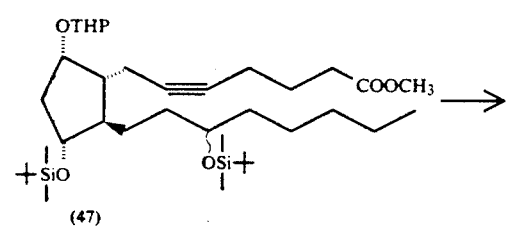
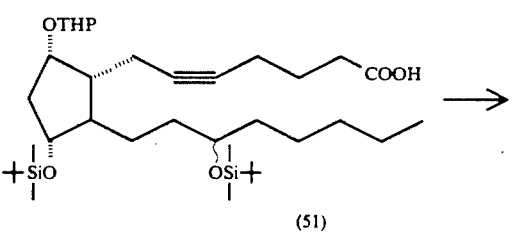
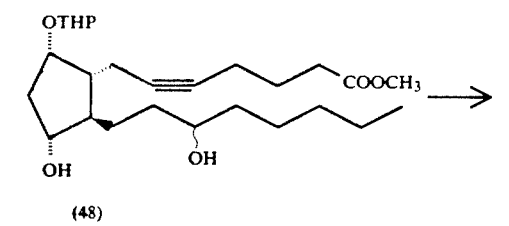
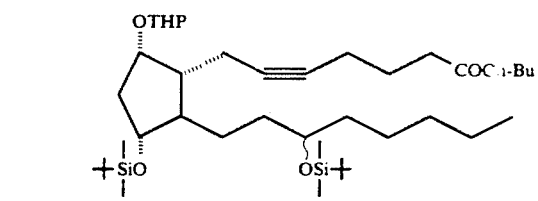
Synthetic Chart 7
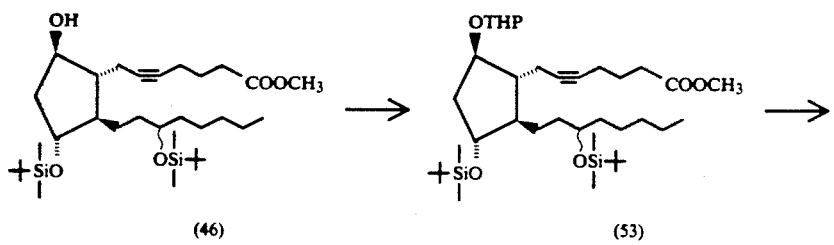

-continued
Synthetic Chart 7
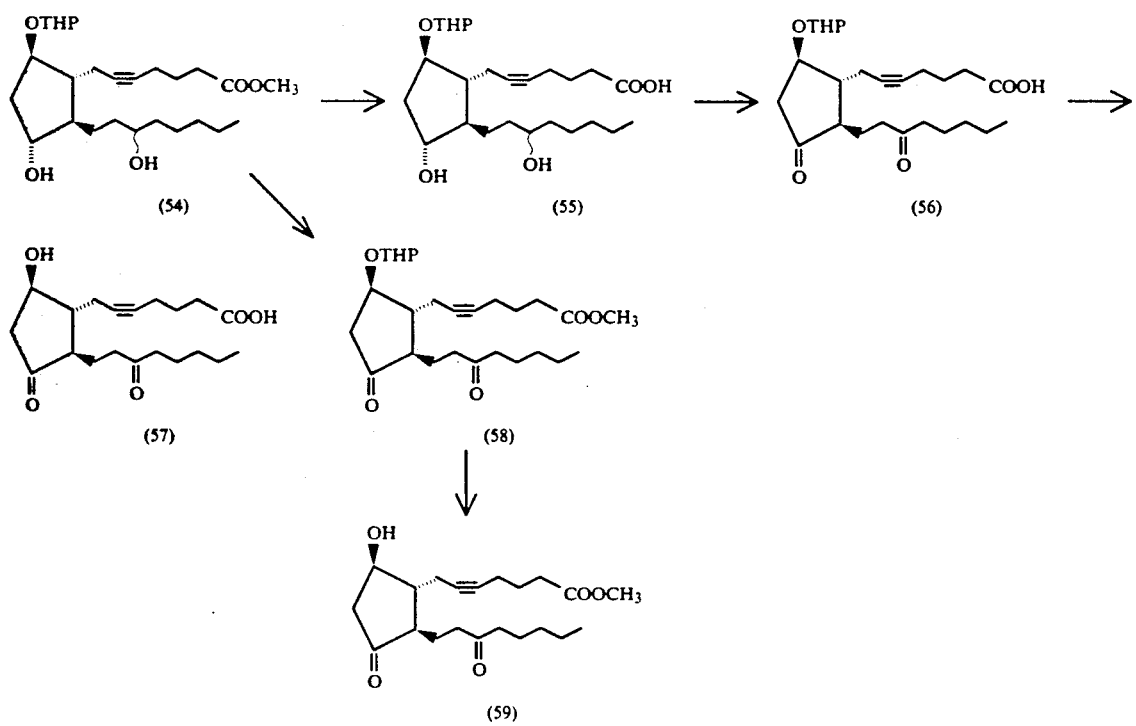
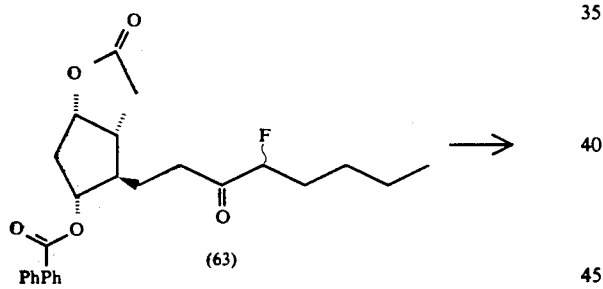
Synthetic Chart 8
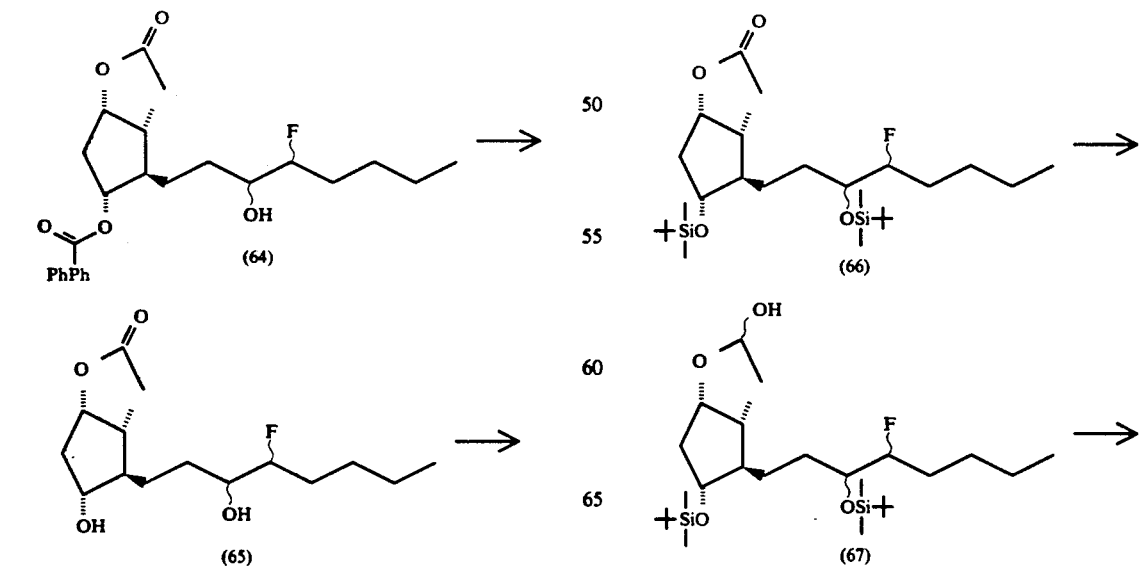
-continued
Synthetic Chart 8

-continued
Synthetic Chart 8

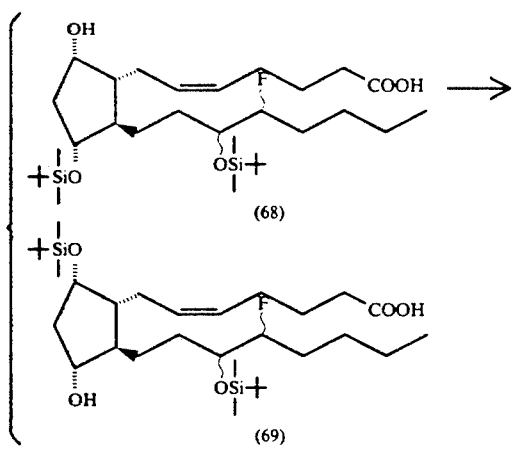
(68)
(69)

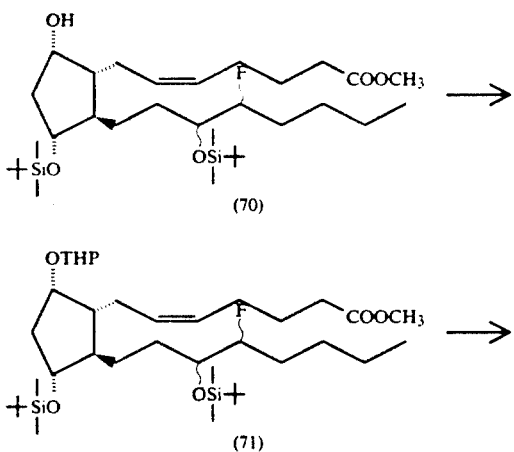
(70)
(71)

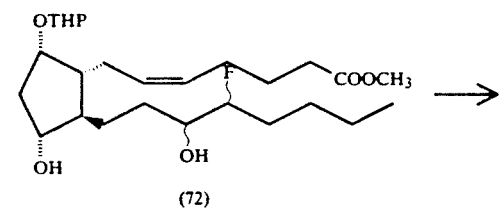
(72)

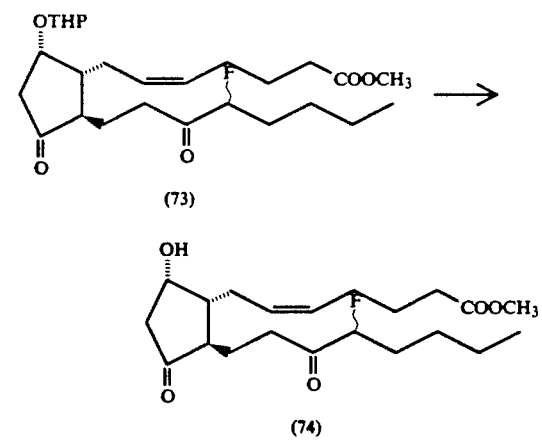
(73)
(74)

What is claimed is:
1. A prostaglandin D represented by formula (I):

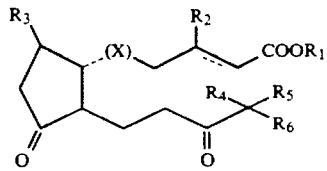

wherein
(X) is

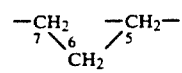    C or

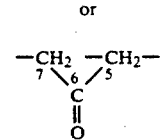    D $R_1$ is hydrogen, a physiologically acceptable salt residue or a physiologically acceptable alkyl ester residue;

$R_2$ is hydrogen or methyl;

$R_3$ is hydroxyl, methyl or hydroxymethyl;

$R_4$ and $R_5$, which may be the same or different, each represents hydrogen, methyl or halogen;

when at least 1 of $R_4$ and $R_5$ is halogen, $R_6$ is $C_{1-9}$ alkyl which may be branched or contain a double bond or is a $C_{1-9}$ alkyl containing a $C_{1-2}$ alkoxy substituent; or when $R_4$ and $R_5$ are independently hydrogen or methyl, $R_6$ is $C_{6-9}$ alkyl which may be branched or contain a double bond or a $C_{1-9}$ alkyl containing a $C_{1-2}$ alkoxy substituent;

and wherein carbons at the 2-3 positions may have double bond.

2. A prostaglandin D of claim 1, in which $R_6$ is a $C_4$-$C_9$ alkyl group.

3. A prostaglandin D of claim 1, in which $R_6$ is a $C_2$-$C_6$ alkyl group having a methoxy or ethoxy substituent.

4. A prostaglandin D of claim 1, in which $R_1$ is a $C_1$-$C_4$ alkyl group.

5. A prostaglandin D of claim 1, in which $R_4$ and/or $R_5$ is methyl or fluorine atom.

6. A prostaglandin D of claim 1, in which the $R_1$ ester residue is selected from the group consisting of a $C_{1-4}$ alkyl group, an alkylsilicon group and a tetrahydroxypyran group.

7. A prostaglandin D of claim 1, in which at least one of $R_4$ and $R_5$ is a halogen atom.

8. A prostaglandin D of claim 7, in which the halogen atom is a fluorine atom.

9. A prostaglandin D of claim 8, in which both $R_4$ and $R_5$ are fluorine atoms.

10. A prostaglandin D of claim 8, in which one of $R_4$ and $R_5$ is a fluorine atom and the other is a hydrogen atom.

11. A prostaglandin D of claim 1, in which at least one of $R_4$ and $R_5$ is a methyl group.

12. A prostaglandin D of claim 11, in which both $R_4$ and $R_5$ are a methyl.

13. A prostaglandin D of claim 11, in which one of $R_4$ and $R_5$ is a methyl group and the other is a hydrogen atom.

14. A prostaglandin D of claim 1, in which $R_6$ is $-(CH_2)_4-C_{1-5}$ alkyl.

15. A prostaglandin D of claim 1, in which $R_6$ is a $C_6$ alkyl group.

16. A tranquilizer or soporific containing an amount effective as a tranquilizer or soporific of a prostaglandin D of claim 1 as an active ingredient, and a pharmaceutically acceptable carrier.

17. A tranquilizer or soporific containing an amount effective as a tranquilizer or soporific of a prostaglandin D of claim 2 as an active ingredient, and a pharmaceutically acceptable carrier.

18. A tranquilizer or soporific containing an amount effective as a tranquilizer or soporific of a prostaglandin D of claim 3 as an active ingredient, and a pharmaceutically acceptable carrier.

19. A tranquilizer or soporific containing an amount effective as a tranquilizer or soporific of a prostaglandin D of claim 4 as an active ingredient, and a pharmaceutically acceptable carrier.

20. A tranquilizer or soporific containing an amount effective as a tranquilizer or soporific of a prostaglandin D of claim 5 as an active ingredient, and a pharmaceutically acceptable carrier.

21. A tranquilizer or soporific containing an amount effective as a tranquilizer or soporific of a prostaglandin D of claim 6 as an active ingredient, and a pharmaceutically acceptable carrier.

22. A tranquilizer or soporific containing an amount effective as a tranquilizer or soporific of a prostaglandin D of claim 7 as an active ingredient, and a pharmaceutically acceptable carrier.

23. A tranquilizer or soporific containing an amount effective as a tranquilizer or soporific of a prostaglandin D of claim 8 as an active ingredient, and a pharmaceutically acceptable carrier.

24. A tranquilizer or soporific containing an amount effective as a tranquilizer or soporific of a prostaglandin D of claim 9 as an active ingredient, and a pharmaceutically acceptable carrier.

25. A tranquilizer or soporific containing an amount effective as a tranquilizer or soporific of a prostaglandin D of claim 10 as an active ingredient, and a pharmaceutically acceptable carrier.

26. A tranquilizer or soporific containing an amount effective as a tranquilizer or soporific of a prostaglandin D of claim 11 as an active ingredient, and a pharmaceutically acceptable carrier.

27. A tranquilizer or soporific containing an amount effective as a tranquilizer or soporific of a prostaglandin D of claim 12 as an active ingredient, and a pharmaceutically acceptable carrier.

28. A tranquilizer or soporific containing an amount effective as a tranquilizer or soporific of a prostaglandin D of claim 13 as an active ingredient, and a pharmaceutically acceptable carrier.

29. A tranquilizer or soporific containing an amount effective as a tranquilizer or soporific of a prostaglandin D of claim 14 as an active ingredient, and a pharmaceutically acceptable carrier.

30. A tranquilizer or soporific containing an amount effective as a tranquilizer or soporific of a prostaglandin D of claim 15 as an active ingredient, and a pharmaceutically acceptable carrier.

31. A process for treating a patient in need of a tranquilizer which comprises administering to said patient a tranquilizing effective amount of a compound of claim 1.

32. A process for treating a patient in need of a tranquilizer which comprises administering to said patient a tranquilizing effective amount of a compound of claim 2.

33. A process for treating a patient in need of a tranquilizer which comprises administering to said patient a tranquilizing effective amount of a compound of claim 3.

34. A process for treating a patient in need of a tranquilizer which comprises administering to said patient a tranquilizing effective amount of a compound of claim 4.

35. A process for treating a patient in need of a tranquilizer which comprises administering to said patient a tranquilizing effective amount of a compound of claim 5.

36. A process for treating a patient in need of a tranquilizer which comprises administering to said patient a tranquilizing effective amount of a compound of claim 6.

37. A process for treating a patient in need of a tranquilizer which comprises administering to said patient a tranquilizing effective amount of a compound of claim 7.

38. A process for treating a patient in need of a tranquilizer which comprises administering to said patient a tranquilizing effective amount of a compound of claim 8.

39. A process for treating a patient in need of a tranquilizer which comprises administering to said patient a tranquilizing effective amount of a compound of claim 9.

40. A process for treating a patient in need of a tranquilizer which comprises administering to said patient a tranquilizing effective amount of a compound of claim 10.

41. A process for treating a patient in need of a tranquilizer which comprises administering to said patient a tranquilizing effective amount of a compound of claim 11.

42. A process for treating a patient in need of a tranquilizer which comprises administering to said patient a tranquilizing effective amount of a compound of claim 12.

43. A process for treating a patient in need of a tranquilizer which comprises administering to said patient a tranquilizing effective amount of a compound of claim 13.

44. A process for treating a patient in need of a tranquilizer which comprises administering to said patient a tranquilizing effective amount of a compound of claim 14.

45. A process for treating a patient in need of a tranquilizer which comprises administering to said patient a tranquilizing effective amount of a compound of claim 15.

46. A process for treating a patient in need of a soporific which comprises administering to said patient a soporific effective amount of a compound of claim 1.

47. A process for treating a patient in need of a soporific which comprises administering to said patient a soporific effective amount of a compound of claim 2.

48. A process for treating a patient in need of a soporific which comprises administering to said patient a soporific effective amount of a compound of claim 3.

49. A process for treating a patient in need of a soporific which comprises administering to said patient a soporific effective amount of a compound of claim 4.

50. A process for treating a patient in need of a soporific which comprises administering to said patient a soporific effective amount of a compound of claim 5.

51. A process for treating a patient in need of a soporific which comprises administering to said patient a soporific effective amount of a compound of claim 6.

52. A process for treating a patient in need of a soporific which comprises administering to said patient a soporific effective amount of a compound of claim 7.

53. A process for treating a patient in need of a soporific which comprises administering to said patient a soporific effective amount of a compound of claim 8.

54. A process for treating a patient in need of a soporific which comprises administering to said patient a soporific effective amount of a compound of claim 9.

55. A process for treating a patient in need of a soporific which comprises administering to said patient a soporific effective amount of a compound of claim 10.

56. A process for treating a patient in need of a soporific which comprises administering to said patient a soporific effective amount of a compound of claim 11.

57. A process for treating a patient in need of a soporific which comprises administering to said patient a soporific effective amount of a compound of claim 12.

58. A process for treating a patient in need of a soporific which comprises administering to said patient a soporific effective amount of a compound of claim 13.

59. A process for treating a patient in need of a soporific which comprises administering to said patient a soporific effective amount of a compound of claim 14.

60. A process for treating a patient in need of a soporific which comprises administering to said patient a soporific effective amount of a compound of claim 15.

* * * * *